United States Patent
Johnson et al.

(10) Patent No.: US 11,135,387 B2
(45) Date of Patent: Oct. 5, 2021

(54) PATIENT INTERFACE

(71) Applicant: Fisher & Paykel Healthcare Limited, Auckland (NZ)

(72) Inventors: Chelsea Erin Johnson, Auckland (NZ); Robert Andrew David Milne, Auckland (NZ); Michael Paul Ronayne, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 301 days.

(21) Appl. No.: 15/562,131

(22) PCT Filed: Mar. 30, 2016

(86) PCT No.: PCT/NZ2016/050050
§ 371 (c)(1),
(2) Date: Sep. 27, 2017

(87) PCT Pub. No.: WO2016/159783
PCT Pub. Date: Oct. 6, 2016

(65) Prior Publication Data
US 2018/0078727 A1    Mar. 22, 2018

Related U.S. Application Data

(60) Provisional application No. 62/140,316, filed on Mar. 30, 2015, provisional application No. 62/159,915, (Continued)

(51) Int. Cl.
*A61M 16/06* (2006.01)
*A61M 25/02* (2006.01)
*A61M 16/00* (2006.01)

(52) U.S. Cl.
CPC .... *A61M 16/0666* (2013.01); *A61M 16/0605* (2014.02); *A61M 16/0688* (2014.02);
(Continued)

(58) Field of Classification Search
CPC .............. A61J 15/0053; A61J 15/0003; A61M 2025/0266; A61M 2025/0246;
(Continued)

(56) References Cited

U.S. PATENT DOCUMENTS

| 5,292,312 A | 3/1994 | Delk et al. |
| 5,682,881 A | 11/1997 | Winthrop et al. |

(Continued)

FOREIGN PATENT DOCUMENTS

| GB | 2520356 | 5/2015 |
| WO | WO 1998/044973 | 10/1998 |

(Continued)

OTHER PUBLICATIONS

International Search Report, Application No. PCT/NZ2016/050050, dated Aug. 15, 2016, in 6 pages.

*Primary Examiner* — Kendra D Carter
*Assistant Examiner* — Arielle Wolff
(74) *Attorney, Agent, or Firm* — Knobbe, Martens, Olson & Bear, LLP

(57) ABSTRACT

A patient interface includes a first body that rests on a first portion of a patient's face, a second body that rests on a second portion of the patient's face, and a bridge linking the first and second bodies. The patient interface includes an attachment structure that couples with a complementary fixation structure positioned on the patient's face to secure the patient interface to the patient's face. The complementary fixation structure can be configured to assist in retaining a feeding tube in position relative to the patient's face or to the patient interface.

31 Claims, 26 Drawing Sheets

Related U.S. Application Data filed on May 11, 2015, provisional application No. 62/258,998, filed on Nov. 23, 2015.

(52) U.S. Cl.
CPC ......... *A61M 25/02* (2013.01); *A61M 16/0057* (2013.01); *A61M 2025/022* (2013.01); *A61M 2025/0226* (2013.01); *A61M 2025/0266* (2013.01); *A61M 2209/088* (2013.01); *A61M 2210/0606* (2013.01)

(58) Field of Classification Search
CPC .............. A61M 16/0666; A61M 25/02; A61M 16/0605; A61M 16/0688; A61M 2209/088; A61M 16/0057; A61M 2025/022; A61M 2025/0226; A61M 2210/0606
See application file for complete search history.

(56) References Cited

U.S. PATENT DOCUMENTS

| | | |
|---|---|---|
| 2005/0197628 A1 | 9/2005 | Roberts et al. |
| 2010/0292649 A1 | 11/2010 | Morrison et al. |
| 2012/0029435 A1 | 2/2012 | Gutierrez Del Rio |
| 2015/0090255 A1* | 4/2015 | Gulliver .............. A61J 15/0053 128/202.15 |
| 2016/0030696 A1* | 2/2016 | Klenner ............ A61M 16/0683 128/207.18 |
| 2017/0281895 A1* | 10/2017 | Kessler ............. A61M 16/0683 |

FOREIGN PATENT DOCUMENTS

| | | |
|---|---|---|
| WO | WO 2008/148085 A1 | 12/2008 |
| WO | WO 2013/157960 | 10/2013 |

\* cited by examiner

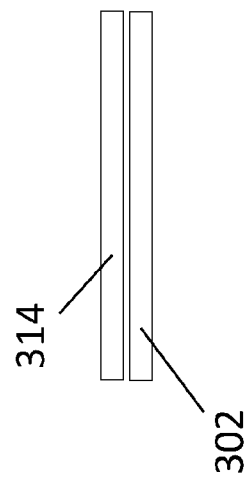
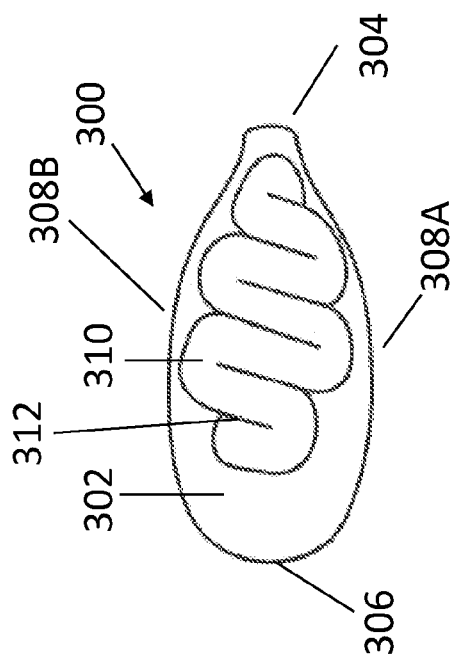
FIGURE 5A
FIGURE 5B
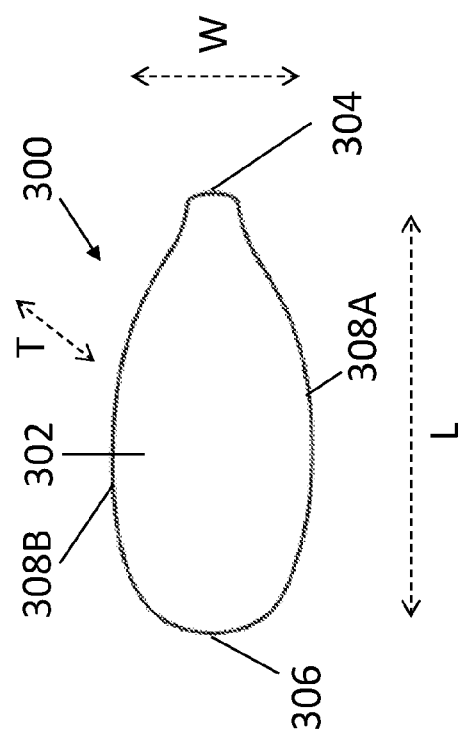
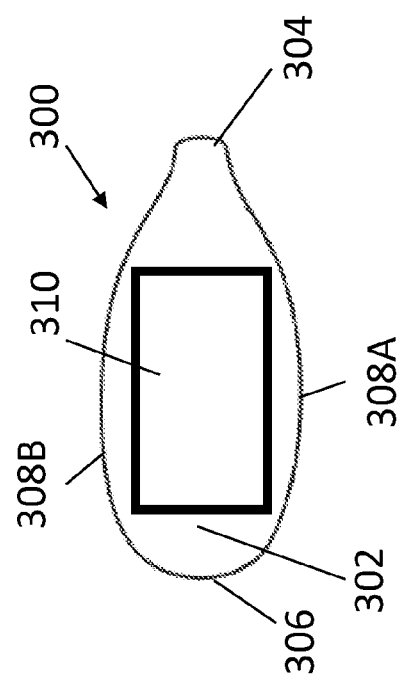
FIGURE 5C
FIGURE 5D

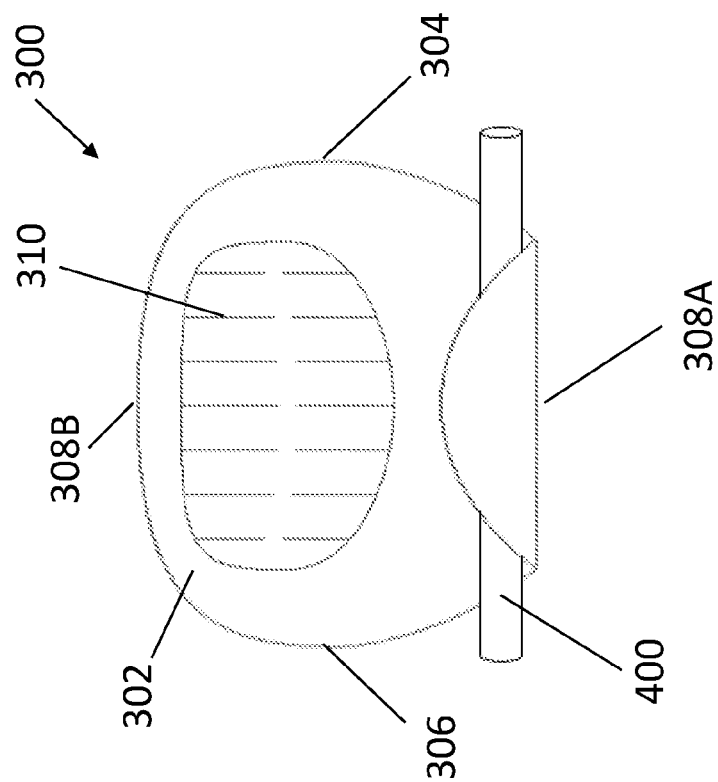
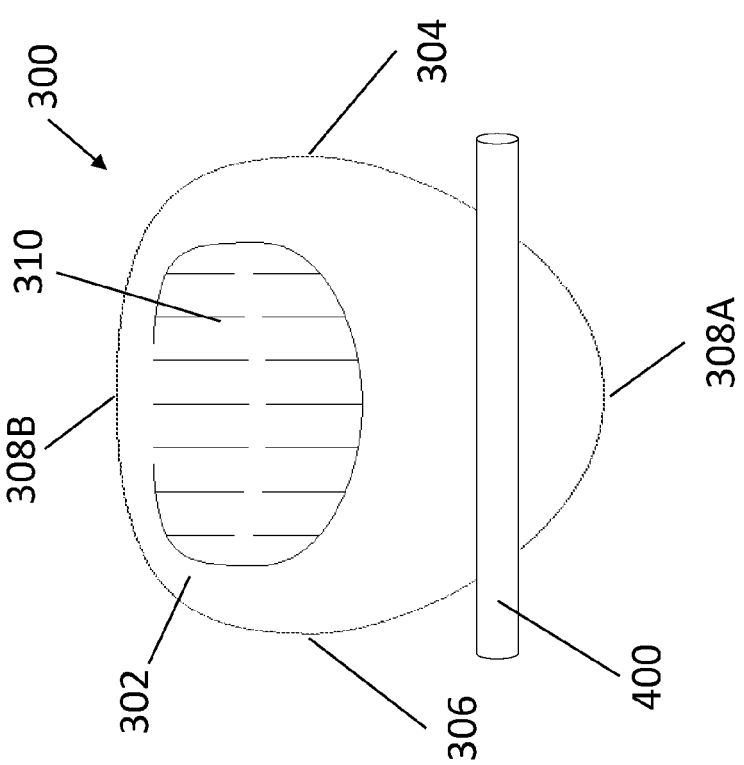

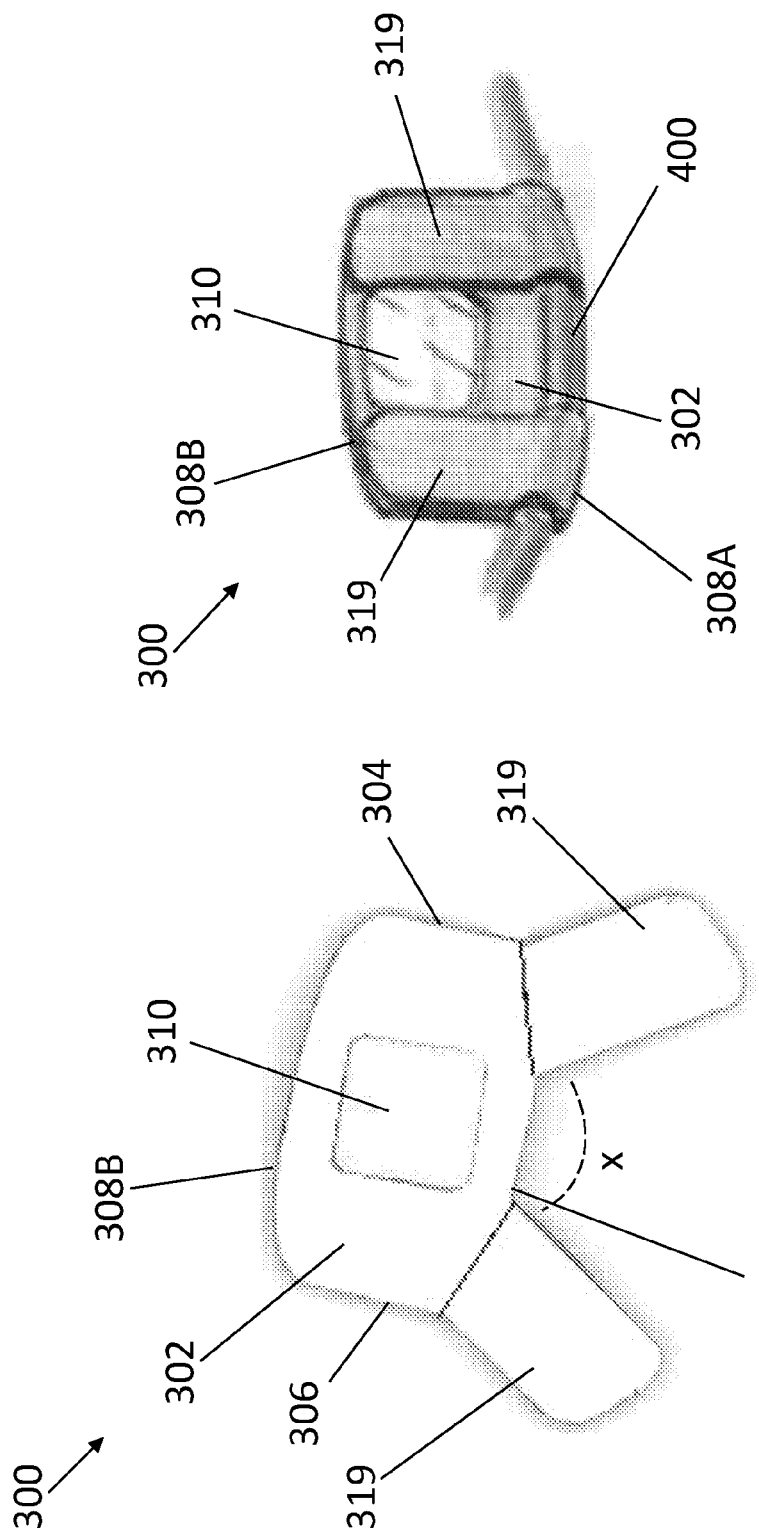

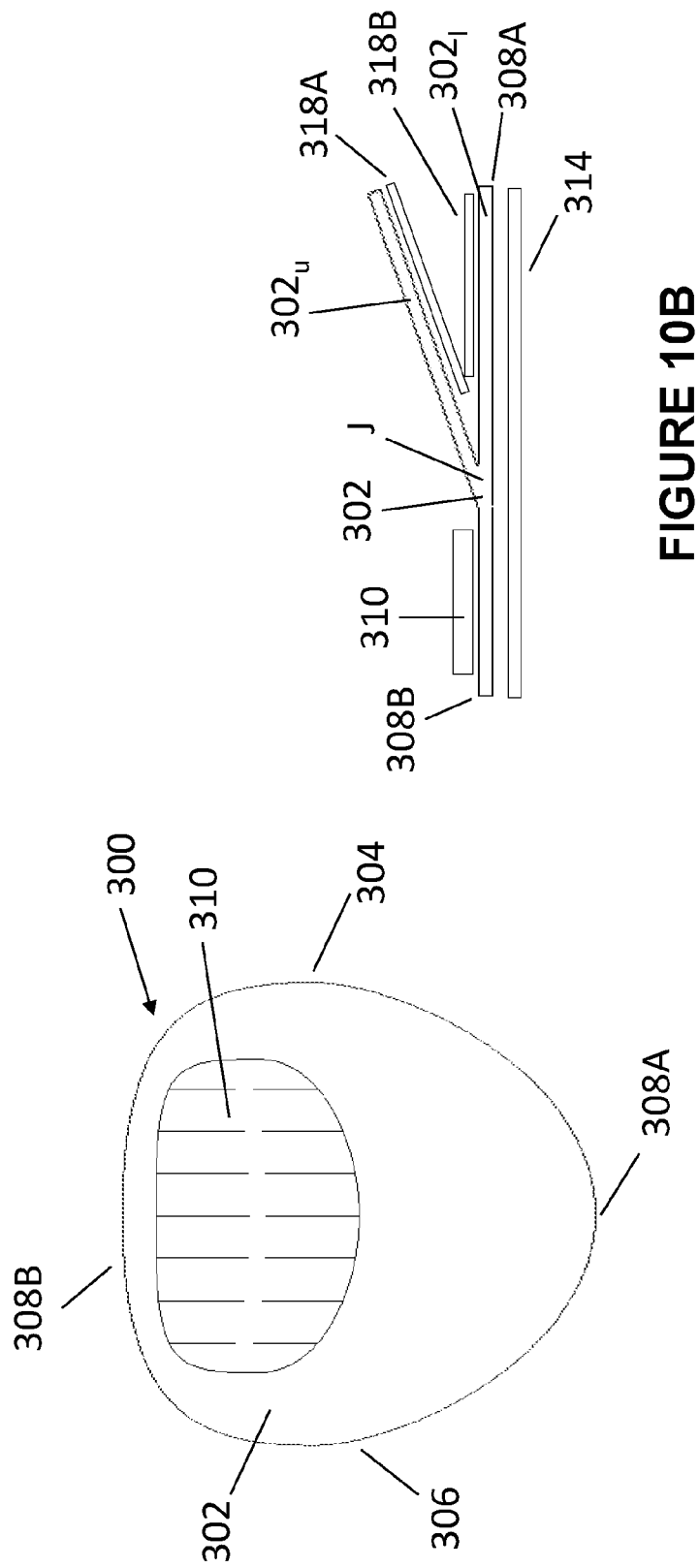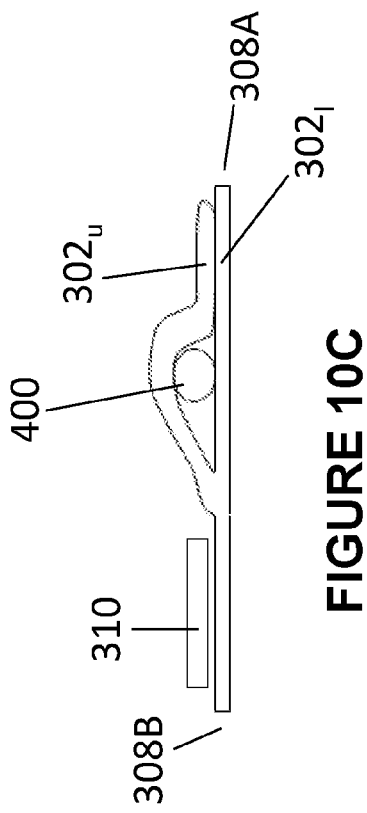

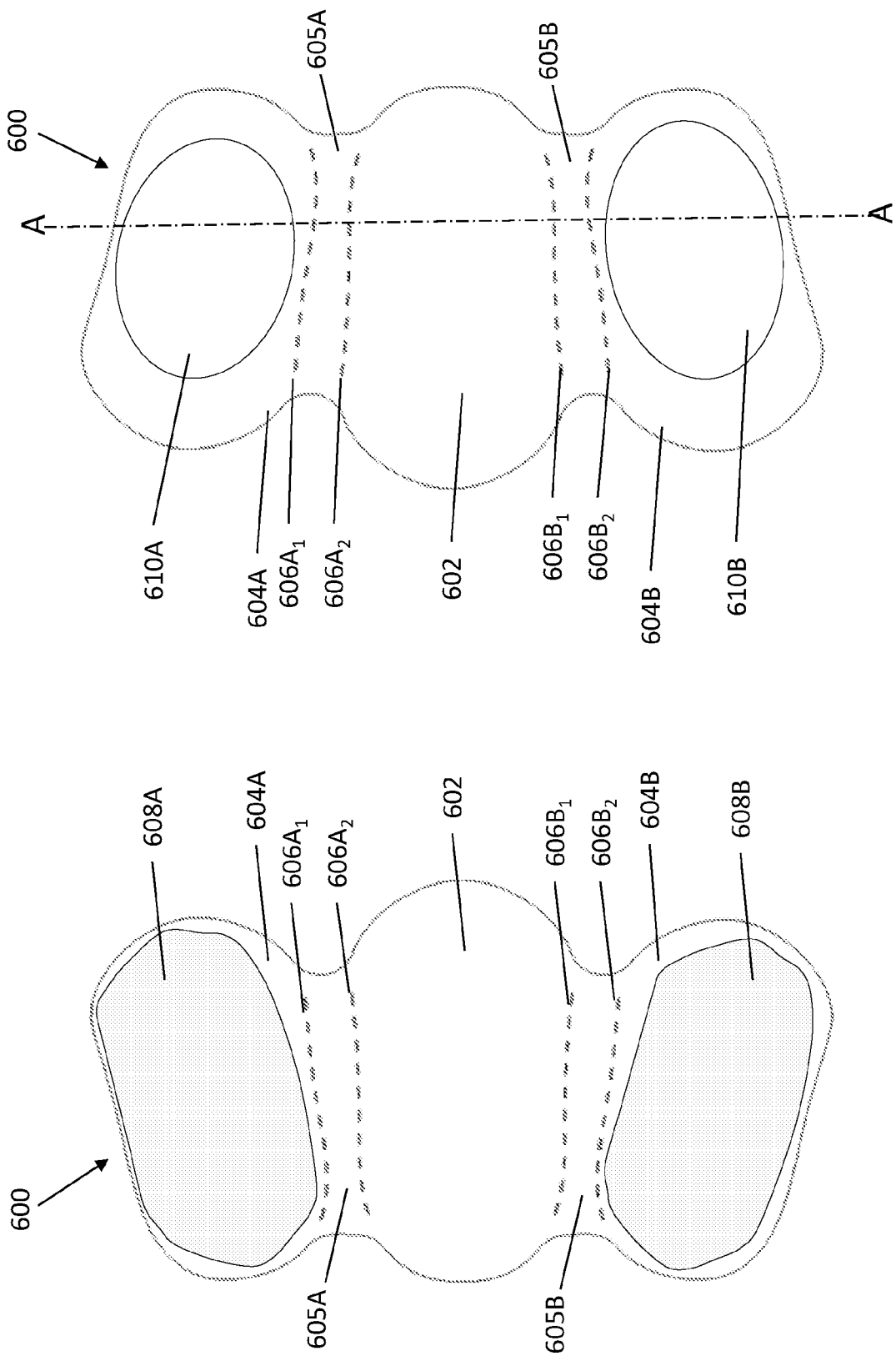

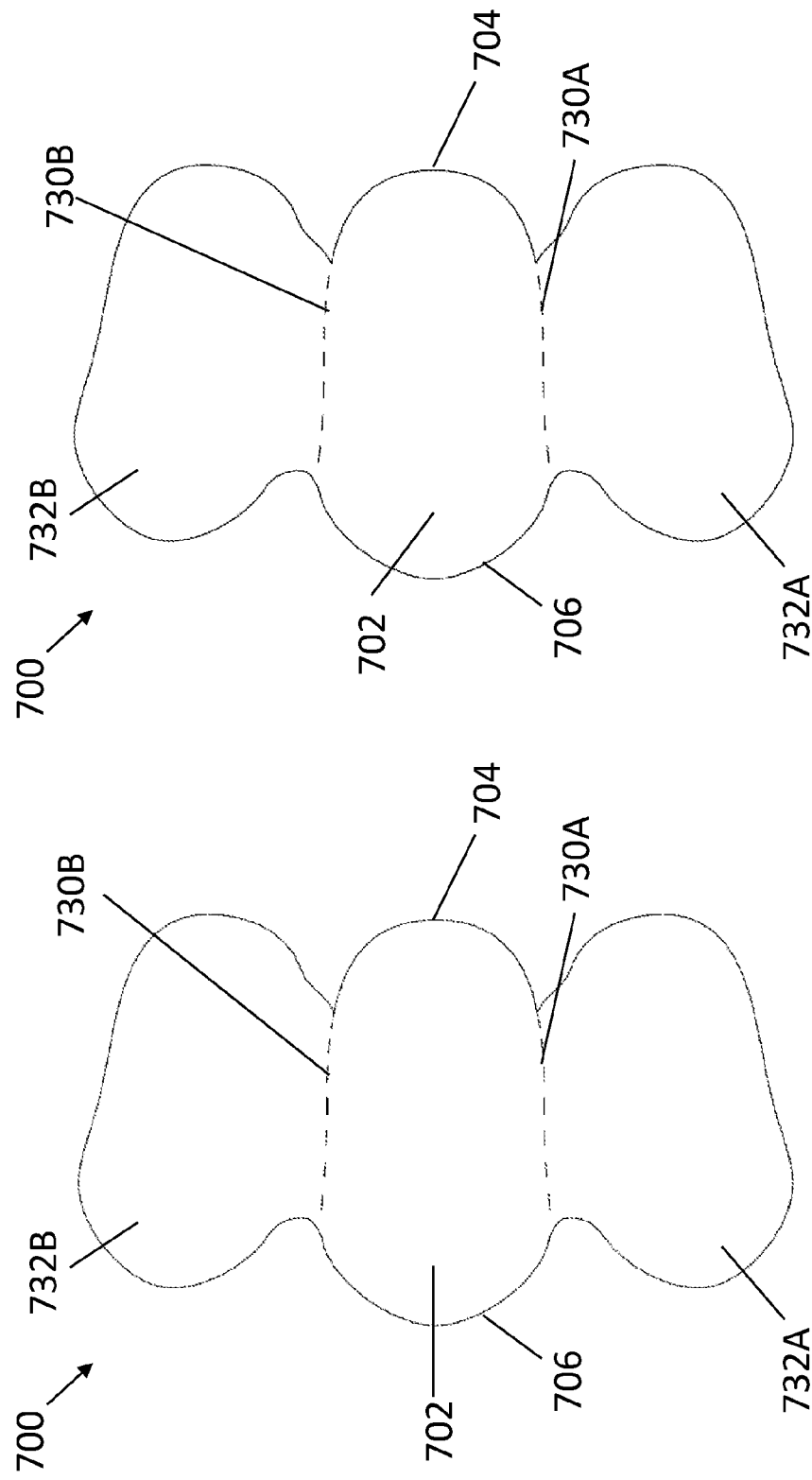

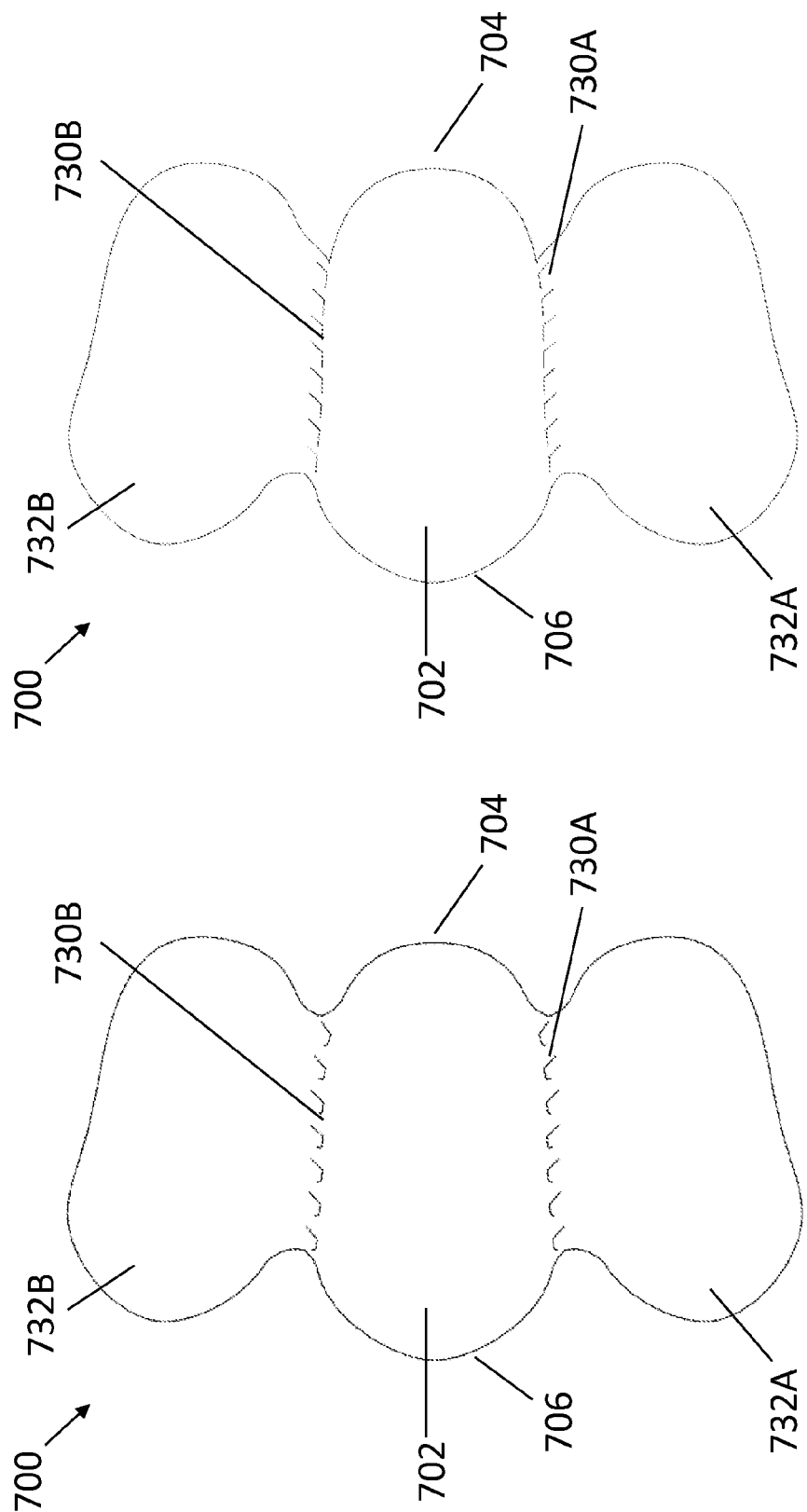

PATIENT INTERFACE

BACKGROUND

Technical Field

The present disclosure generally relates to respiratory therapy. More particularly, the present disclosure relates to a patient interface for providing respiratory therapy.

Description of the Related Art

A patient dealing with respiratory illness, for example chronic obstructive pulmonary disease (COPD), can have difficulty engaging in effective respiration. This difficulty may be the result of a variety of causes, including a breakdown of lung tissue, dysfunctions of the small airways, excessive accumulation of sputum, infection, genetic disorders, or cardiac insufficiency. With some respiratory illnesses, it is useful to provide a patient with a therapy that can improve the ventilation of the patient. The patient can be provided with high flow therapy using a respiratory therapy system that includes a gases source, a patient interface that may be used to transmit gases to an airway of a patient, and a conduit extending between the gases source and the patient interface. The patient interface is typically not sealed. The gases may be heated and humidified before delivery to the patient.

Obstructive Sleep Apnea (OSA) is a sleep disorder in which muscles that normally hold open the airway collapse, temporarily sealing the airway. The sleep pattern of an OSA sufferer is characterized by repeated sequences of snoring, breathing difficulty, lack of breathing, waking with a start, and then returning to sleep. The respiratory therapy of Continuous Positive Airway Pressure (CPAP) can be used to splint the airway and reduce or eliminate the occurrence of OSA. The patient can be provided with CPAP therapy using a respiratory therapy system that includes a gases source, a patient interface that may be used to transmit gases to an airway of a patient, and a conduit extending between the gases source and the patient interface. The patient interface is typically sealed. The gases may be heated and humidified before delivery to the patient.

SUMMARY

With some patients, food or nutritional supplements are best delivered to the patient via a feeding tube. In many cases, tubing can be passed through the patient's nose and threaded into, for example, the stomach for nasogastric tubing, the jejunum for nasojejunal tubing, or other portions of the digestive tract. Other tubes may be passed into the patient's nose to deliver medication or to measure a characteristic of the patient. Similarly, tubing can be passed through the patient's mouth and threaded into, for example, the stomach for orogastric tubing, the jejunum for orojejunal tubing, or other portions of the digestive tract, or to deliver medication or measure a characteristic of the patient. In some configurations, tubes can be placed into both the nose and mouth of a patient. A patient interface, such as a nasal cannula, can be used to deliver respiratory gases to the patient. Managing the amount of space available on the patient's face for tubing and a patient interface can become difficult, especially for infants or neonates or other patients with limited facial space or small facial geometries. Adjustment or removal of the tubing without disruption of the delivery of the respiratory therapy via the patient interface, or adjustment or removal of the patient interface without disruption of the delivery of nutrients or medication or of some other function via the tubing, can be challenging. Solutions to the above difficulties, or systems or apparatus that provide a useful alternative, are sought.

The systems, methods and devices described herein have innovative aspects, no single one of which is indispensable or solely responsible for their desirable attributes. Without limiting the scope of the claims, some of the advantageous features will now be summarized.

In accordance with certain features, aspects and advantages of one or more of the embodiments disclosed herein, a fixation structure is disclosed. The fixation structure is adapted to cooperate with a patient interface to secure the patient interface on a face of a patient. The fixation structure comprises a body having first and second regions. The first region is adapted to adhere to the patient's face. The second region comprises first and second portions. The first portion comprises a first fastener adapted to couple with a complementary second fastener of the patient interface. The second portion is adapted to secure a tube.

In some configurations, the second portion is adapted to secure the tube within a nasal or oral airway of the patient. In some configurations, the second portion is adapted to encapsulate the tube. In some configurations, the body comprises a rounded rectangular shape. In some configurations, the first fastener comprises either hook or loop portions. In some configurations, the second portion comprises an elongate section that is flexible and configured to fold to encapsulate and secure the tube. In some configurations, the second portion comprises an elongate portion that extends below the fixation structure, the elongate portion configured to fold upon itself to secure the tube.

Additionally, in accordance with certain features, aspects and advantages of one or more of the embodiments disclosed herein, a fixation structure is disclosed. The fixation structure is adapted to cooperate with a patient interface to secure the patient interface on a face of a patient. The fixation structure comprises a triangular body having opposed first and second regions. The first region is adapted to adhere to the patient's face. The second region comprises first and second portions. The first portion comprises a first fastener adapted to couple with a complementary second fastener of the patient interface. The second portion is adapted to secure a tube.

In some configurations, the triangular body has a shape substantially similar to a Reuleaux triangle. In some configurations, the triangular body comprises rounded edges. In some configurations, the second portion is adapted to encapsulate the tube.

Additionally, in accordance with certain features, aspects and advantages of one or more of the embodiments disclosed herein, a fixation structure is disclosed. The fixation structure is adapted to cooperate with a patient interface to secure the patient interface on a face of a patient. The fixation structure comprises a body having opposed first and second regions. The first region is adapted to adhere to the patient's face. The second region comprises first and second portions. The first portion comprises a first fastener adapted to couple with a complementary second fastener of the patient interface. The second portion is adapted to secure a tube. The second portion comprises a pair of legs projecting outwardly from the body. The legs are adapted to encapsulate a portion of the tube to secure the tube.

In some configurations, the legs are substantially parallel to each other. In some configurations, the legs are offset from one another at an angle of less than about 180 degrees. In some configurations, the legs are offset from one another at an angle of less than about 90 degrees. In some configurations, the legs are offset from one another at an angle of less than about 60 degrees.

Additionally, in accordance with certain features, aspects and advantages of one or more of the embodiments disclosed herein, a fixation structure is disclosed. The fixation structure is adapted to cooperate with a patient interface to secure the patient interface on a face of a patient. The fixation structure comprises a body having opposed first and second regions. The first region is adapted to adhere to the patient's face. The second region comprises first and second portions. The first portion comprises a first fastener adapted to couple with a complementary second fastener of the patient interface. The second portion is adapted to secure a tube. The second portion comprises a shape that substantially complements an edge of the first fastener in use.

In some configurations, the shape is a substantially contoured shape. In some configurations, the contoured shape comprises two projections configured to encapsulate the tube. In some such configurations, the projections are formed by a recess.

In some configurations, the second portion comprises a recess or cutout that imparts the complementary shape. In some configurations, the second portion is adapted to encapsulate the tube.

In some configurations, the tube can comprise a feeding tube, for example but not limited to a nasogastric, nasojejunal, orogastric, or orojejunal tube.

In some configurations, the fixation structure comprises a backing layer adapted to protect the second portion.

Additionally, in accordance with certain features, aspects and advantages of one or more of the embodiments disclosed herein, a fixation structure is disclosed. The fixation structure is adapted to cooperate with a patient interface to secure the patient interface on a face of a patient. The fixation structure comprises a body having opposed first and second regions. The first region is adapted to be secured to the patient's face. The body comprises a flexible portion and at least one separable extension adapted to secure a tube.

In some configurations, the separable extension is separated and attached to a different part of the patient's face, and the body comprising a second extension that can be pivoted or folded to secure the tube to the body. In some configurations, the body includes an anchoring section to attach the patient interface to the body. In some configurations, the separable extension includes an anchoring section to anchor or support the patient interface. In some configurations, the body supports a portion of the patient interface, and the separable extension is separated from the body and attached to a portion of the face spaced away from the body, the separable extension also supporting the patient interface. In some such configurations, the patient interface is an unsealed interface, such as a nasal cannula.

In some configurations, the at least one separable extension comprises a weakened section. In some configurations, the at least one separable extension is linked to the body via a perforated section.

In some configurations, the at least one separable extension comprises a first region adapted to secure the tube and a second region adapted to secure the patient interface. In some such configurations, the first region of the at least one separable extension comprises an adhesive layer. In some such configurations, the adhesive layer is adapted to adhere to the tube. In some configurations, the second region of the at least one separable extension comprises a first fastener adapted to couple with a complementary second fastener of the patient interface.

In some configurations, the body comprises a pair of substantially opposed separable extensions. In some configurations, the body comprises a first edge adapted to face towards the patient's nose or mouth in use, a second edge adapted to face away from the patient's nose or mouth in use, and opposed third and fourth edges extending between the first and second edges. In some such configurations, the pair of separable extensions are linked to the third and fourth edges of the body. In some configurations, the body comprises a first edge adapted to face towards the patient's nose or mouth in use, and a second edge adapted to face away from the patient's nose or mouth in use. In some such configurations, the pair of separable extensions are linked to the first and second edges of the body.

Additionally, in accordance with certain features, aspects and advantages of one or more of the embodiments disclosed herein, a fixation structure is disclosed. The fixation structure is adapted to cooperate with a patient interface to secure the patient interface on a face of a patient. The fixation structure comprises a body having first and second separable extensions, where each of the separable extensions comprises a tube securement portion adapted to be secured to a tube and a fixation element adapted to be secured to the patient interface.

Additionally, in accordance with certain features, aspects and advantages of one or more of the embodiments disclosed herein, a patient interface system is disclosed. The patient interface system comprises a patient interface comprising an attachment structure secured to a patient-facing portion of the patient interface, the attachment structure adapted to couple with a fixation structure secured to the face to fasten the patient interface to the face; and a fixation structure. The fixation structure may be the same or similar to the fixation structures described in the passages above or elsewhere in the specification with reference to the accompanying figures.

In some configurations, the patient interface comprises a first body adapted to rest on a first portion of the patient's face, a second body adapted to rest on a second portion of the patient's face, and a bridge linking the first and second bodies. In some configurations, the attachment structure is secured to patient-facing portions of the first and/or second bodies. In some configurations, the patient interface comprises a nasal cannula, nasal mask, oral mask, oro-nasal mask, full face mask, unsealed oro-nasal interface, nasal pillows mask, endotracheal tube, or other such respiratory interface.

Additionally, in accordance with certain features, aspects and advantages of one or more of the embodiments disclosed herein, a fixation structure is disclosed. The fixation structure is configured to fix a patient interface upon a patient. The fixation structure comprises a body with a first region and second region, the first region configured to contact a portion of a patient's face, and the second region configured to face outward from the patient's face. The body comprises first and second extensions, the first and second extensions being pivotably attached to the body, the first extension being separable from the body, and the second extension configured, in use, to pivot relative to the body and to secure a feeding tube to the body.

In some configurations, the first extension, in use, can be separated from the body and positioned on another portion of the patient's face. In some configurations, the first extension comprises a first region adapted to secure the tube and a second region adapted to secure the patient interface. In some configurations, the first region of the first extension comprises an adhesive layer. In some configurations, the adhesive layer is adapted to adhere to the tube. In some configurations, the second region of the first extension comprises a first fastener adapted to interface with a complementary second fastener of the patient interface. In some configurations, the first and second extensions comprise a pair of substantially opposed separable extensions.

In some configurations, the body comprises a first edge adapted to face towards a nose or mouth of the patient in use, a second edge adapted to face away from the nose or mouth of the patient in use, and opposed third and fourth edges extending between the first and second edges. In some such configurations, the pair of separable extensions are linked to the third and fourth edges of the body.

In some configurations, the body comprises a first edge adapted to face towards a nose or mouth of the patient in use, and a second edge adapted to face away from the nose or mouth of the patient in use. In some such configurations, the pair of separable extensions are linked to the first and second edges of the body.

Additionally, in accordance with certain features, aspects and advantages of one or more of the embodiments disclosed herein, a fixation structure for use with a patient interface is disclosed. The fixation structure comprises a body configured to be adhered to a portion of a patient's face. The body comprises at least one separable section that can be separated from the body. The separable section is connected to the body by a weakened joint.

In some configurations, the body comprises at least one pivotable section extending from the body. In some such configurations, the pivotable section is configured to pivot and connect to a non-patient-contacting region of the body. In some configurations, the pivotable section is configured to pivot to secure a feeding tube to the body.

Additionally, in accordance with certain features, aspects and advantages of one or more of the embodiments disclosed herein, a fixation structure assembly for securing a tube to a patient is disclosed. The fixation structure assembly comprises a body, a first extension, and a second extension. The body comprises a top region and a bottom region, the bottom region configured to adhere to the patient's face. The first extension is connected with a first lateral side of the body via a first intermediate region. The first extension comprises a first adhesive portion. The first extension is configured to fold over the body about a first pivot axis such that the first extension substantially overlaps with, and adheres to, the body. The second extension is connected with a second lateral side of the body via a second intermediate region. The second extension comprises a second adhesive portion and a second fixation element. The second extension is configured to fold over the body about a second pivot axis such that the second extension substantially overlaps with, and adheres to, the body.

In some configurations, the first extension comprises a first fixation element configured to couple with a first corresponding fixation element of a patient interface. In some such configurations, the first extension is configured such that, when the first extension is overlapped with the body, the first fixation element faces outward from the patient's face. In some configurations, the second extension comprises a second fixation element configured to couple with a second corresponding fixation element of the patient interface. In some such configurations, the second extension is configured such that, when the second extension is overlapped with the body, the second fixation element faces outward from the patient's face.

In some configurations, the first intermediate region comprises a first perforation configured to allow the first extension to be separated from the body. In some configurations, the second intermediate region comprises a second perforation configured to allow the second extension to be separated from the body. In some configurations, the first and second lateral sides are on opposite lateral sides of the body. In some configurations, the body further comprises a longitudinal axis, and the first pivot axis is substantially parallel with the longitudinal axis. In some configurations, the second pivot axis is substantially parallel with the longitudinal axis. In some configurations, at least one of the first and second intermediate areas is configured to receive the tube.

In some configurations, the first extension further comprises a bearing portion configured to enable a user to engage the bearing portion with a finger or instrument. In some configurations, the bearing portion comprises a tab. In some configurations, the fixation structure assembly comprises a backing strip comprising one or more folds.

Additionally, in accordance with certain features, aspects and advantages of one or more of the embodiments disclosed herein, a method of manufacturing a fixation structure assembly adapted to secure a tube to a patient is disclosed. The method comprises obtaining a substrate portion comprising a body comprising a top face and bottom face, a first extension portion that extends from a first lateral side of the body, the first extension portion comprising a top face and bottom face, and a second extension portion that extends from a second lateral side of the body, the second extension portion comprising a top face and bottom face; applying an adhesive to the top face of the first extension portion; attaching a first fixation element to the bottom face of the first extension portion; applying an adhesive to the top face of the second extension portion; attaching a second fixation element to the bottom face of the second extension portion; and applying an adhesive to the bottom face of the body.

In some configurations, the method comprises perforating a first intermediate region between the body and the first extension portion; and perforating a second intermediate region between the body and the second extension portion.

Additionally, in accordance with certain features, aspects and advantages of one or more of the embodiments disclosed herein, a fixation structure assembly for securing a tube to a patient is disclosed. The fixation structure assembly comprises a body configured to adhere to the patient's face, and an extension configured to wrap around the tube and to connect with the body, thereby securing the tube between the extension and the body. The extension is configured to separate from the body in response to activation of a breakable portion, thereby enabling the tube to be separated from the body while maintaining the tube in the patient.

In some configurations, the breakable portion comprises a perforated portion. In some configurations, the extension is configured to secure the tube by folding the extension over the tube and adhering the extension to the body. In some configurations, the fixation structure comprises a second extension connected with the body.

Additionally, in accordance with certain features, aspects and advantages of one or more of the embodiments disclosed herein, a method of disconnecting a fixation structure from a tube while maintaining a distal end of the tube inside a patient's body is disclosed. The fixation structure comprises a body and an extension, the body connected with the patient's face, and the tube secured between the extension and the body. The method comprises grasping the tube; moving the fixation structure relative to the tube in a direction non-parallel with a longitudinal axis of the tube; activating a breakable portion of the fixation structure; and separating the fixation structure from the tube.

In some configurations, activating the breakable portion of the fixation structure comprises breaking a row of perforations. In some configurations, activating the breakable portion of the fixation structure comprises breaking a first row of perforations and breaking a second row of perforations. In some configurations, activating a breakable portion of the fixation structure further comprises separating, from the body and from the remainder of the extension, a portion of the extension that is positioned between the first and second rows of perforations. In some such configurations, separating the fixation structure from the tube comprises removing the body from the tube and, separately, removing the extension from the tube. In some configurations, the method comprises disconnecting the body of the fixation structure from the patient's face.

Additionally, in accordance with certain features, aspects and advantages of one or more of the embodiments disclosed herein, a method of replacing a fixation structure for securing a tube to a patient's face while maintaining a distal end of the tube inside the patient's body is disclosed. The method comprises disconnecting a first fixation structure and connecting a second fixation structure, wherein connecting the second fixation structure comprises connecting a body of the second fixation structure to the patient's face; placing the tube along the body of the second fixation structure; wrapping an extension of the second fixation structure circumferentially around a portion of the tube; and securing the tube between the extension of the second fixation structure and the body of the second fixation structure. The first fixation structure may be the same or similar to the fixation structures described in the passages above or elsewhere in the specification with reference to the accompanying figures.

In some configurations, securing the tube between the extension of the second fixation structure and the body of the second fixation structure comprises adhering the extension of the second fixation structure to the body of the second fixation structure.

Additionally, in accordance with certain features, aspects and advantages of one or more of the embodiments disclosed herein, a fixation structure adapted to cooperate with a patient interface to secure the patient interface on a face of a patient is disclosed. The fixation structure comprises a body and a first extension connected with the body. The body comprises a first region adapted to adhere to the patient's face and a second region adapted to face away from the patient's face. The second region comprises a non-adhesive portion. The first extension is configured to fold over at least a portion of the body. The first extension comprises an adhesive portion configured to adhere with the second region of the body when the first extension is folded over the body.

In some configurations, the fixation structure comprises a second extension connected with the body. In some configurations, the second extension is configured to fold over at least a portion of the body. In some configurations, the second extension comprises a non-adhesive portion configured to adhere with the second region of the body when the second extension is folded over the body. In some configurations, the first extension and the second extension are positioned on generally opposite lateral sides of the body.

In some configurations, the fixation structure comprises a perforation configured to allow the first extension to be torn apart from the body. In some such configurations, the perforation is located at the connection between the first extension and the body. In some configurations, the fixation structure comprises a second perforation configured to allow the second extension to be torn apart from the body. In some such configurations, the second perforation is located at the connection between the first extension and the body. In some configurations, the fixation structure comprises a fixation element adapted to cooperate with the patient interface. In some such configurations, the fixation element comprises a hooked pad or a looped pad.

Additionally, in accordance with certain features, aspects and advantages of one or more of the embodiments disclosed herein, a fixation structure for securing a patient interface on a patient's face is disclosed. The fixation structure comprises a body comprising opposed first and second regions. The first region comprises an adhesive to adhere to the patient's face. The second region comprises first and second portions. The first portion comprises a first fastener to attach to a complementary second fastener of the patient interface. The second portion is adapted to secure a tube.

The second portion may be adapted to encapsulate the tube. The second portion may comprise a flexible elongate section adapted to fold to encapsulate and secure the tube. The second portion may comprise an elongate portion that extends below the fixation element, the elongate portion adapted to fold upon itself to secure the tube. The first fastener may comprise either hook or loop portions of a hook-and-loop attachment system.

The body may comprise a substantially rectangular shape. The body may comprise a substantially triangular shape. The substantially rectangular or triangular shape of the body may comprise rounded corners. The second portion may comprise a shape that substantially complements an edge of the first fastener. The shape of the second portion may comprise a substantially contoured shape. The second portion may comprise a pair of legs projecting outwardly from the body, the legs adapted to encapsulate a portion of the tube to secure the tube. The legs may be substantially parallel. The legs may be offset from one another at an angle of less than 90 degrees. The legs may be offset from one another at an angle of more than 90 degrees.

The tube may be a feeding tube. The fixation structure may comprise a backing layer to protect the second portion.

Additionally, in accordance with certain features, aspects and advantages of one or more of the embodiments disclosed herein, a fixation structure for securing a patient interface on a patient's face is disclosed. The fixation structure comprises a body comprising at least one separable extension and opposed first and second regions, the first region comprising an adhesive to adhere to the patient's face. The at least one separable extension is adapted to secure a tube.

The at least one separable extension may comprise a weakened section. The at least one separable extension may be attached to the body via a perforated section. The at least one separable extension may comprise a first portion adapted to secure the tube and a second portion adapted to secure the patient interface. The first portion of the at least one separable extension may comprise an adhesive layer to adhere to the tube. The second portion of the at least one separable extension may comprise a first fastener to attach to a complementary second fastener of the patient interface. The at least one separable extension may comprise a pair of separable extensions.

The body may comprise a first edge facing towards the patient's nose or mouth in use, a second edge facing away from the patient's nose or mouth in use, and opposed third and fourth edges extending between the first and second edges, wherein the pair of separable extensions are attached to the third and fourth edges of the body via perforated sections. The body may comprise a first edge facing towards the patient's nose or mouth in use and a second edge facing towards the patient's nose or mouth in use, wherein the pair of separable extensions are attached to the first and second edges of the body via perforated sections.

Additionally, in accordance with certain features, aspects and advantages of one or more of the embodiments disclosed herein, a fixation structure configured to fix a patient interface upon a patient is disclosed. The fixation structure comprises a body. The body comprises first and second regions. The first region is configured to contact a portion of a patient's face. The second region is configured to face outward from the patient's face. The body comprises first and second extensions. The first and second extensions are pivotably attached to the body. The first extension is separable from the body. The second extension is configured to pivot relative to the body and to secure a tube to the body.

The first extension may be configured to be separated from the body and positioned on another portion of the patient's face. The first extension may comprise a first region adapted to secure the tube and a second region adapted to secure the patient interface. The first region of the first extension may comprise an adhesive layer. The adhesive layer may be adapted to adhere to the tube. The second region of the first extension may comprise a first fastener adapted to attach to a complementary second fastener of the patient interface. The first and second extensions may comprise a pair of substantially opposed separable extensions.

The body may comprise a first edge adapted to face towards the patient's nose or mouth, a second edge adapted to face away from the patient's nose or mouth, and opposed third and fourth edges extending between the first and second edges, wherein the pair of separable extensions are attached to the third and fourth edges of the body via perforated sections. The body may comprise a first edge adapted to face towards the patient's nose or mouth and a second edge adapted to face away from the patient's nose or mouth, wherein the pair of separable extensions are attached to the first and second edges of the body via perforated sections.

Additionally, in accordance with certain features, aspects and advantages of one or more of the embodiments disclosed herein, a fixation structure for securing a patient interface to a patient's face is disclosed. The fixation structure comprises a body comprising an adhesive to adhere to a portion of the patient's face and at least one separable section that can be separated from the body. The at least one separable section is connected to the body by a weakened joint.

The body may comprise at least one pivotable section extending from the body. The at least one pivotable section may be configured to pivot and connect to a non-patient-contacting region of the body. The at least one pivotable section may be configured to pivot to secure a tube to the body.

Additionally, in accordance with certain features, aspects and advantages of one or more of the embodiments disclosed herein, a fixation structure for securing a patient interface on a patient's face is disclosed. The fixation structure comprises a body comprising a first region comprising an adhesive to adhere to the patient's face and a second region adapted to face away from the patient's face, the second region comprising a non-adhesive portion. The body comprises a first extension connected with the body, the first extension configured to fold over at least a portion of the body, the first extension comprising an adhesive portion to adhere with the second region of the body when the first extension is folded over the body.

The fixation structure may comprise a second extension. The second extension may be connected with the body. The second extension may be configured to fold over at least a portion of the body. The second extension may comprise a non-adhesive portion configured to adhere with the second region of the body when the second extension is folded over the body. The first extension and the second extension may be positioned on generally opposite lateral sides of the body.

The fixation structure may comprise a first perforation configured to allow the first extension to be torn apart from the body. The first perforation may be located at the connection between the first extension and the body. The fixation structure may comprise a second perforation configured to allow the second extension to be torn apart from the body. The second perforation may be located at the connection between the second extension and the body.

The fixation structure may comprise a fixation element adapted to attach to the patient interface. The fixation element may comprise a hooked pad or a looped pad.

Additionally, in accordance with certain features, aspects and advantages of one or more of the embodiments disclosed herein, a patient interface system is disclosed. The patient interface system comprises a patient interface comprising an attachment structure secured to a patient-facing portion of the patient interface, the attachment structure adapted to interface with a fixation structure secured to the face to fasten the patient interface to the face. The patient interface system comprises a fixation structure. The fixation structure may be the same or similar to the fixation structures described in the passages above or elsewhere in the specification with reference to the accompanying figures.

The patient interface may comprise a first body adapted to rest on a first portion of the face, a second body adapted to rest on a second portion of the face, and a bridge linking the first and second bodies. The attachment structure may be secured to patient-facing portions of the first and/or second bodies. The patient interface may comprise an unsealed interface. The patient interface may comprise an sealed interface.

Additionally, in accordance with certain features, aspects and advantages of one or more of the embodiments disclosed herein, a fixation structure assembly for securing a tube to a patient's face is disclosed. The fixation structure assembly comprises a body, a first extension, and a second extension. The body comprises a top face and a bottom face. The bottom face comprises an adhesive to adhere to the patient's face. The first extension is connected with a first lateral side of the body via a first intermediate region. The first extension comprises a first adhesive portion. The second extension is connected with a second lateral side of the body via a second intermediate region. The second extension comprises a second adhesive portion and a second fixation element. The first extension is configured to fold over the body about a first pivot axis such that the first extension substantially overlaps with, and adheres to, the body. The second extension is configured to fold over the body about a second pivot axis such that the second extension substantially overlaps with, and adheres to, the body.

The first extension may comprise a first fixation element to couple with a first corresponding fixation element of a patient interface. The first extension may be configured such that, when the first extension is overlapped with the body, the first fixation element faces outward from the patient's face. The second extension may comprise a second fixation element configured to couple with a second corresponding fixation element of the patient interface. The second extension may be configured such that, when the second extension is overlapped with the body, the second fixation element faces outward from the patient's face. The first intermediate region may comprise a first perforation configured to allow the first extension to be separated from the body. The second intermediate region may comprise a second perforation configured to allow the second extension to be separated from the body.

The first and second lateral sides may be on opposite lateral sides of the body. The body may comprise a longitudinal axis. The first pivot axis may be substantially parallel with the longitudinal axis. The second pivot axis may be substantially parallel with the longitudinal axis. At least one of the first and second intermediate areas may be configured to receive the tube. The first extension may comprise a bearing portion configured to enable a user to engage the bearing portion with a finger or instrument. The bearing portion may comprise a tab. The fixation structure assembly may comprise a backing strip comprising one or more folds.

Additionally, in accordance with certain features, aspects and advantages of one or more of the embodiments disclosed herein, a method of manufacturing a fixation structure assembly for securing a tube to a patient is disclosed. The method comprises obtaining a substrate portion comprising a body comprising a top face and bottom face; a first extension portion that extends from a first lateral side of the body, the first extension portion comprising a top face and bottom face; and a second extension portion that extends from a second lateral side of the body, the second extension portion comprising a top face and bottom face. The method comprises applying an adhesive to the top face of the first extension portion. The method comprises attaching a first fixation element to the bottom face of the first extension portion. The method comprises applying an adhesive to the top face of the second extension portion. The method comprises attaching a second fixation element to the bottom face of the second extension portion. The method comprises applying an adhesive to the bottom face of the body.

The method may comprise perforating a first intermediate region between the body and the first extension portion. The method may comprise perforating a second intermediate region between the body and the second extension portion.

Additionally, in accordance with certain features, aspects and advantages of one or more of the embodiments disclosed herein, a fixation structure assembly for securing a tube to a patient is disclosed. The fixation structure assembly comprises a body comprising an adhesive to adhere to the patient's face and an extension configured to wrap around the tube and to connect with the body, thereby securing the tube between the extension and the body. The extension is configured to separate from the body in response to activation of a breakable portion, thereby enabling the tube to be separated from the body while maintaining the tube in the patient.

The breakable portion may comprise a perforated portion. The extension may be configured to secure the tube by folding the extension over the tube and adhering the extension to the body. The fixation structure assembly may comprise a second extension connected with the body.

Additionally, in accordance with certain features, aspects and advantages of one or more of the embodiments disclosed herein, a method of disconnecting a fixation structure from a tube while maintaining a distal end of the tube inside a patient's body is disclosed. The fixation structure comprises a body and an extension. The body is connected with the patient's face. The tube is secured between the extension and the body. The method comprises grasping the tube, moving the fixation structure relative to the tube in a direction non-parallel with a longitudinal axis of the tube, activating a breakable portion of the fixation structure, and separating the fixation structure from the tube.

Activating the breakable portion of the fixation structure may comprise breaking a row of perforations. Activating the breakable portion of the fixation structure may comprise breaking a first row of perforations and breaking a second row of perforations.

Activating the breakable portion of the fixation structure may comprise separating, from the body and from the remainder of the extension, a portion of the extension that is positioned between the first and second rows of perforations. Separating the fixation structure from the tube may comprise removing the body from the tube and, separately, removing the extension from the tube.

The method may comprise disconnecting the body of the fixation structure from the patient's face.

Additionally, in accordance with certain features, aspects and advantages of one or more of the embodiments disclosed herein, a method of replacing a fixation structure for securing a tube to the patient's face while maintaining a distal end of the tube inside a patient's body is disclosed. The method comprises disconnecting a first fixation structure and connecting a second fixation structure. Disconnecting the first fixation structure comprises a method that may be the same or similar to one or more methods of disconnecting a fixation structure described in the passages above or elsewhere in the specification with reference to the accompanying figures. Connecting a second fixation structure comprises connecting a body of the second fixation structure to the patient's face, placing the tube along the body of the second fixation structure, wrapping an extension of the second fixation structure circumferentially around a portion of the tube, and securing the tube between the extension of the second fixation structure and the body of the second fixation structure.

Securing the tube between the extension of the second fixation structure and the body of the second fixation structure may comprise adhering the extension of the second fixation structure to the body of the second fixation structure.

BRIEF DESCRIPTION OF THE DRAWINGS

Specific embodiments and modifications thereof will become apparent to those skilled in the art from the detailed description herein having reference to the figures that follow.

FIGS. 5A-5D illustrate example embodiments of a fixation structure.

FIGS. 6A-6C illustrate example embodiments of a fixation structure.

FIGS. 8A-8D illustrate example embodiments of a fixation structure.

FIGS. 10A-10C illustrate example embodiments of a fixation structure.

FIGS. 15A-15B illustrate example embodiments of a fixation structure assembly.

FIGS. 17A-17E illustrate example embodiments of a fixation structure.

DETAILED DESCRIPTION

Figure 1:
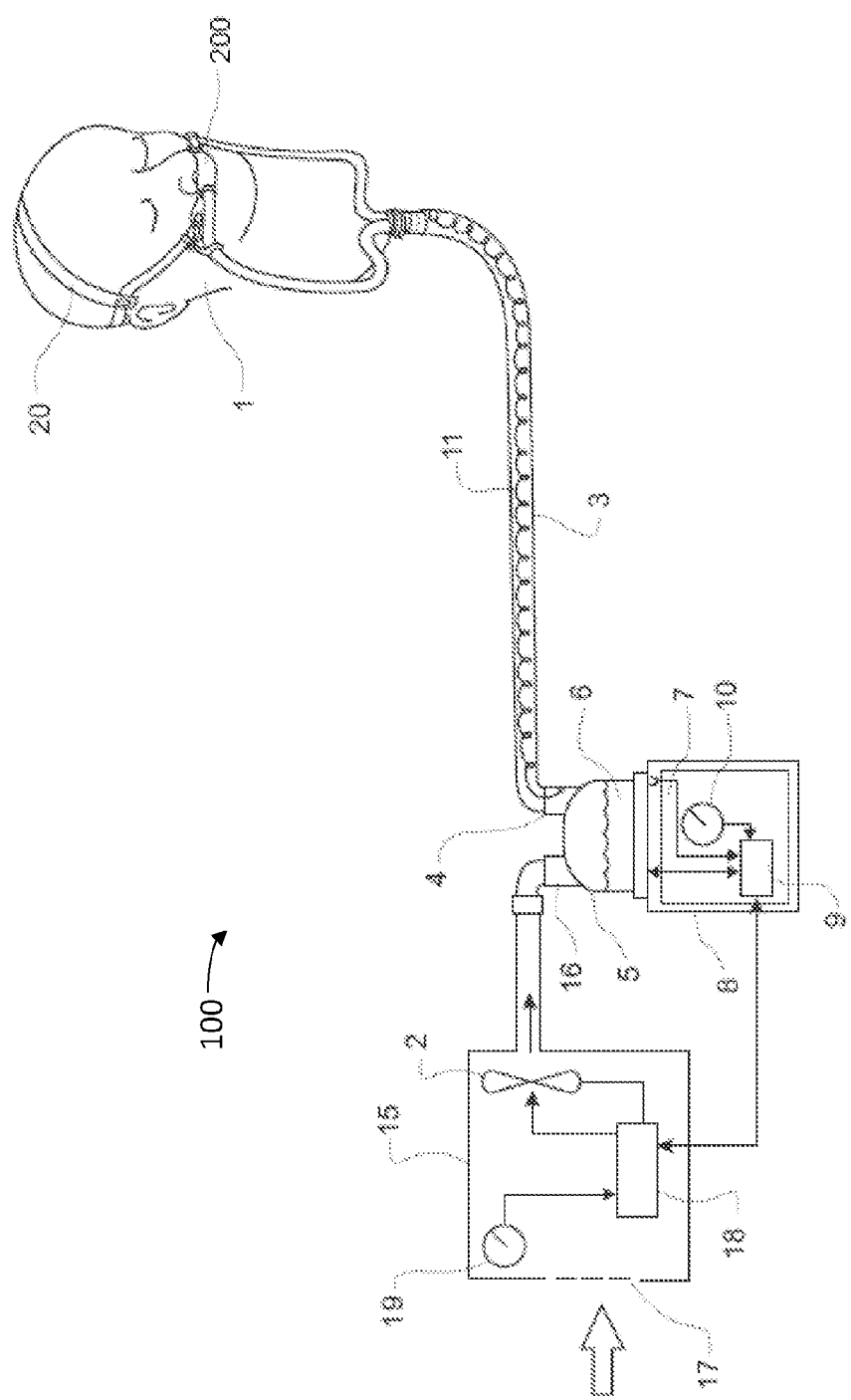
FIG. 1 illustrates an example respiratory therapy system.

FIG. 1 illustrates an example respiratory therapy system 100. A patient 1 is receiving humidified and pressurised gases through a patient interface 200, illustrated in this example as a nasal cannula assembly, connected to a humidified gases transportation pathway or inspiratory conduit 3 that in turn is connected to a humidifier 8 (including a humidification chamber 5) that is supplied with gases from a gases supply means or blower 15 or other appropriate gases supply means. The gases can be supplied from a source that is external to and/or separate from the respiratory therapy system 100, or from a source that is internal to and/or integrated with the respiratory therapy system 100. A headgear 20 is provided to support and retain the patient interface against the patient's face. The inspiratory conduit 3 is connected to an outlet 4 of the humidification chamber 5 which contains a volume of water 6. The humidification chamber 5 is preferably formed from a plastics material and may have a highly heat conductive base (for example an aluminum base) which is in direct contact with a heater plate 7 of the humidifier 8. The humidifier 8 is provided with a control mechanism or electronic controller 9 such as a microprocessor based controller executing computer software commands stored in associated memory. Gases flowing through the inspiratory conduit 3 are passed to the patient by way of the patient interface 200.

The controller 9 receives input from sources or input means, such as a dial 10, through which a user such as a nurse or other healthcare provider may, for example, set a predetermined required value (preset value) of humidity or temperature of the gases supplied to the patient. In response to the user-set humidity or temperature value input via the dial 10 and other possible inputs such as internal sensors that sense gases flow or temperature, or by parameters calculated in the controller 9, the controller 9 determines when (or to what level) to energize the heater plate 7 to heat the water 6 within the humidification chamber 5. As the volume of water 6 within the humidification chamber 5 is heated, water vapor begins to fill the volume of the humidification chamber 5 above the surface of the water 6 and is passed out of the outlet 4 with the flow of gases (for example air) provided by the blower 15 which enters the humidification chamber 5 through an inlet 16. It should be noted that it is possible to determine a relationship between the humidity of the gases in the humidification chamber 5 and the temperature of the heater plate 7. Accordingly, it is possible to utilize the temperature of the heater plate 7 in an algorithm or a look-up table to determine the humidity of the gases.

The blower 15 may be provided with a variable speed pump or fan 2 that draws air or other gases through a blower inlet 17. The speed of the variable speed pump or fan 2 may be controlled by a further control means or electronic controller 18 (or alternatively the function of the controller 18 could be carried out by the controller 9) in response to inputs from the controller 9 and a user-set predetermined required value (preset value) of pressure and/or fan speed via one or more input devices, such as a dial 19.

A heating element 11 may be provided within the conduit 3 to help prevent condensation of the humidified gases within the conduit 3. Such condensation is due to the temperature of the walls of the conduit 3 being close to the ambient temperature, (being the temperature of the surrounding atmosphere) which is usually lower than the temperature of the humidified gases within the conduit 3. The heating element 11 effectively replaces the energy lost from the gases through conduction and convection during transit through the conduit 3. Thus the heating element 11 ensures the gases delivered are at an optimal temperature and humidity.

In the illustrated configurations, the patient interface 200 is a nasal cannula. In some configurations, the patient interface 200 may be a sealing or non-sealing interface. For example, the patient interface 200 may be a nasal mask, an oral mask, an oro-nasal mask, a full face mask, a nasal cannula, an unsealed oro-nasal interface, a nasal pillows mask, an endotracheal tube, a combination of the above or some other gases conveying system or apparatus. In some configurations, the patient interface 200 may be used to deliver respiratory gases in a respiratory therapy system that does not include a humidifier. For example, the patient interface 200 may be used to deliver a mixture of ambient air and oxygen in an oxygen therapy system. Certain features, aspects and advantages of the illustrated nasal cannula may be envisaged in other patient interfaces.

Figure 2:
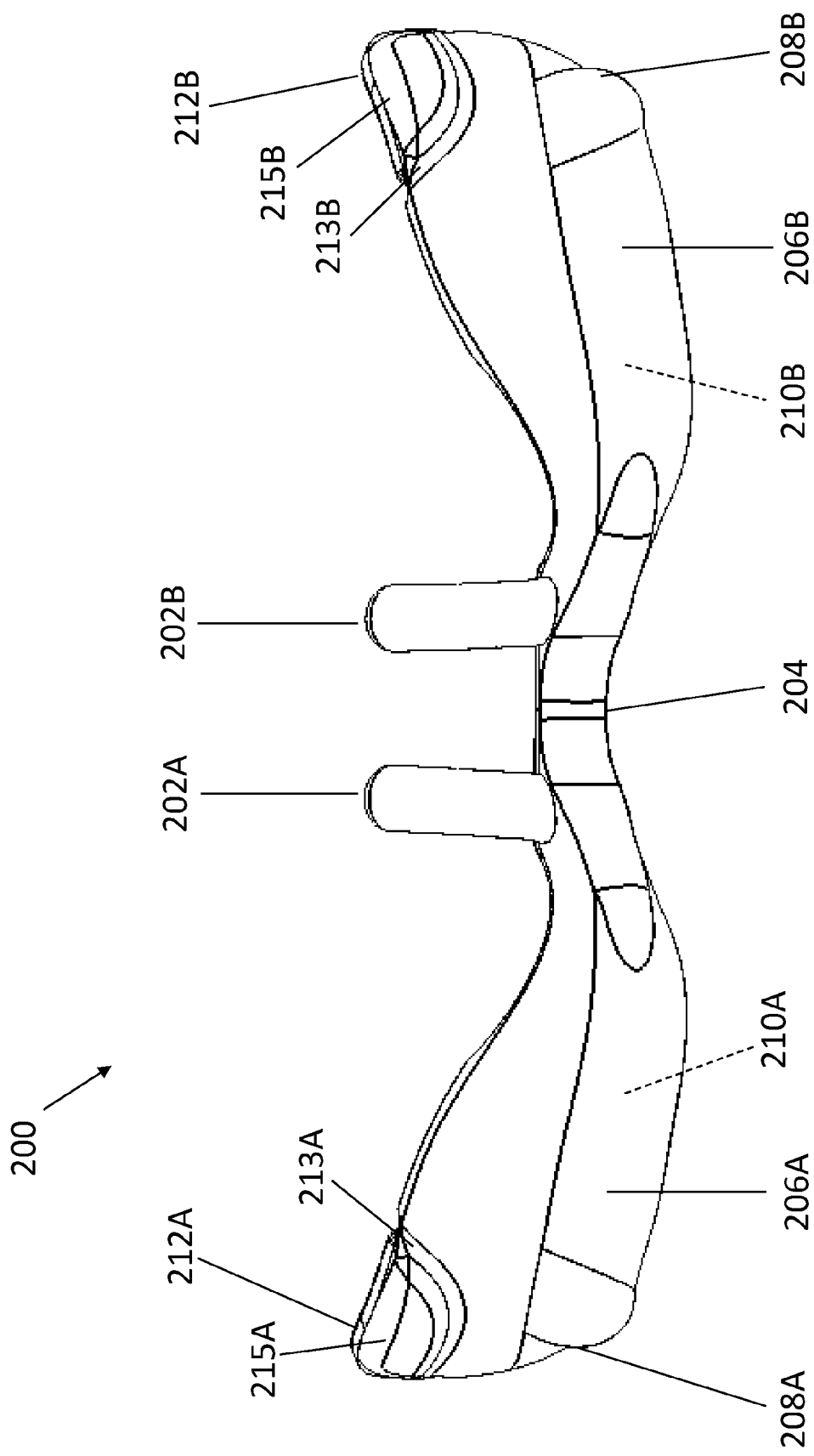
FIG. 2 illustrates a front view of an example embodiment of a patient interface.
Figure 3:
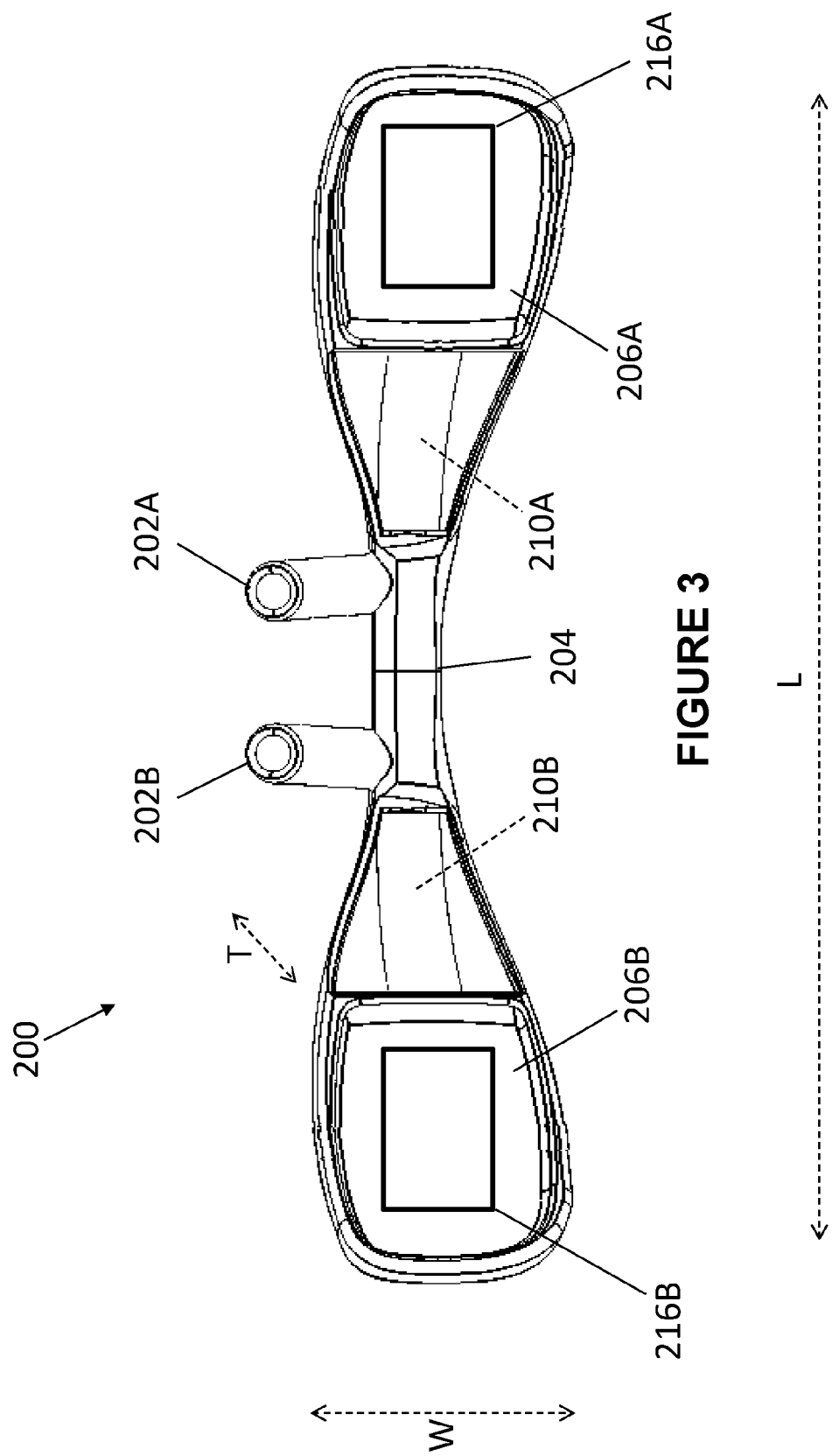
FIG. 3 illustrates a rear view of the patient interface of FIG. 2.
Figure 4:
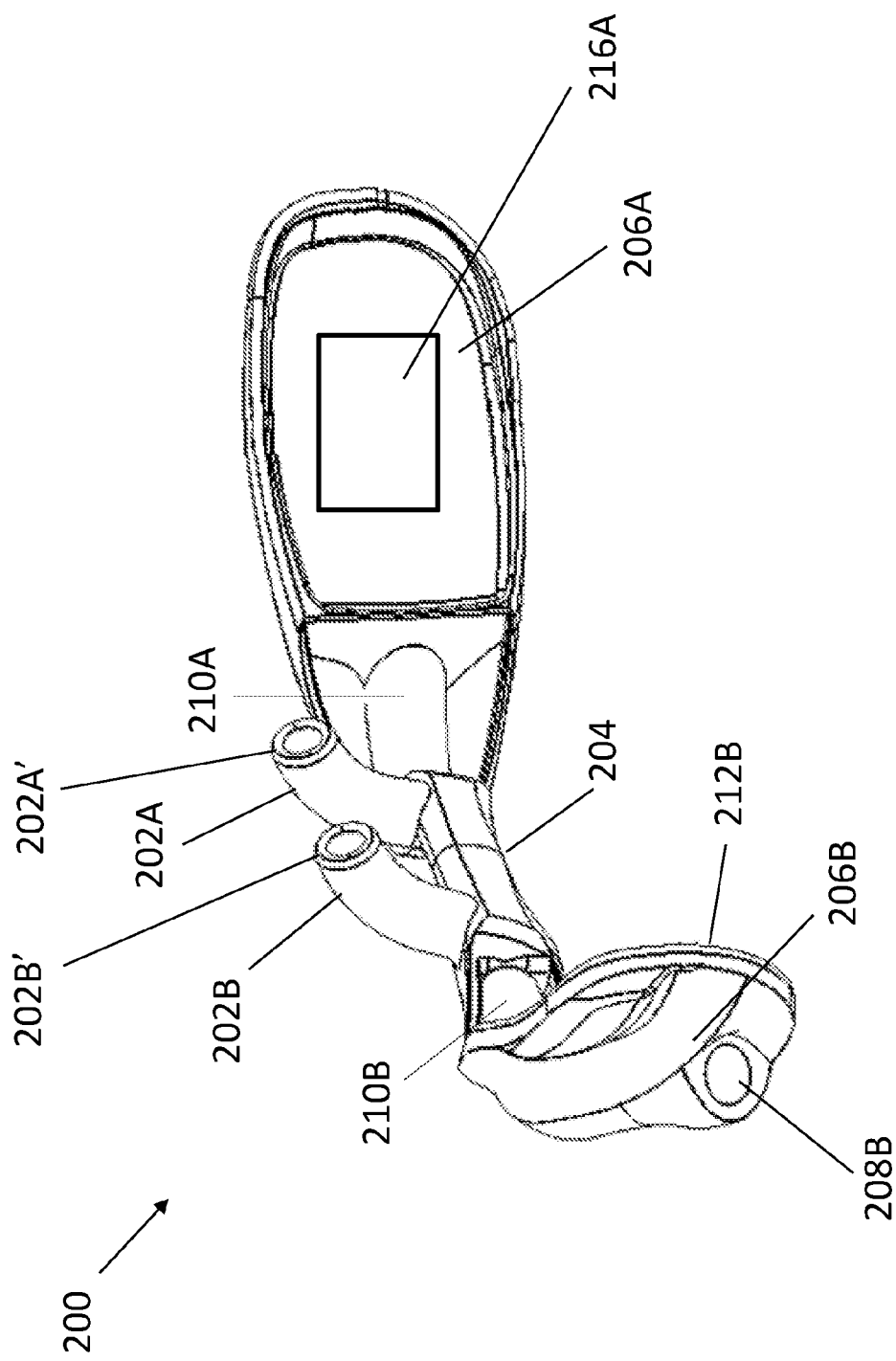
FIG. 4 illustrates a side perspective view of the patient interface of FIG. 2.

FIGS. 2-4 illustrate a non-limiting example embodiment of the patient interface 200. The patient interface 200 can be generally shaped or configured such that it substantially matches the contours of the patient's face. The patient interface 200 includes first and second nasal delivery elements 202A, 202B that rest in the patient's nares in use. The illustrated nasal delivery elements 202A, 202B are substantially tubular and direct gases passing through the patient interface 200 to the patient. The nasal delivery elements 202A, 202B can be shaped and angled such that they generally extend inwardly towards the patient's septum in use. The nasal delivery elements 202A, 202B end in tips 202A', 202B'. In use, the tips 202A', 202B' point towards the back of the patient's head.

In some configurations, the nasal delivery elements 202A, 202B may have different shapes. For example, although the average cross-section of the nasal delivery elements 202A, 202B in the illustrated configurations is substantially circular, in some configurations the cross-section of the nasal delivery elements 202A, 202B could be substantially elliptical, substantially square, or substantially rectangular. In some configurations, the cross-section of the nasal delivery elements 202A, 202B could vary along the length of the nasal delivery elements 202A, 202B. In some configurations, each of the nasal delivery elements 202A, 202B may have different characteristics. For example, the nasal delivery element 202A may be smaller or shorter than the nasal delivery element 202B. In some configurations, only one of the nasal delivery elements 202A, 202B may be used.

The nasal delivery elements 202A, 202B extend from first and second bodies 206A, 206B of the patient interface 200. The bodies 206A, 206B include internal gases delivery lumens 210A, 210B that receive gases from gases inlets 208A, 208B of the bodies 206A, 206B and channel the gases to the nasal delivery elements 202A, 202B. The gases inlets 208A, 208B couple with a pair of gases delivery conduits 218A, 218B (see FIG. 1). In the illustrated configuration, the gases delivery conduits 218A, 218B are integrally formed with or inseparably connected to the gases inlets 208A, 208B. The gases delivery conduits 218A, 218B in turn may be integrally formed or inseparably connected to a gases conduit connector 222. The gases conduit connector 222 may releasably couple with a complementary connector 118 that is in pneumatic communication with a gases conduit 110 (described elsewhere in this disclosure with reference to FIG. 1 as the conduit 3). Other configurations are contemplated. For example, in some configurations, the patient interface 200 may be configured such that the nasal delivery elements 202A, 202B receive gases from one of the internal gases delivery lumens 210A, 210B positioned in one of the bodies 206A, 206B. In some such configurations, the one of the internal gases delivery lumens 210A, 210B may in turn receive gases from one of the gases delivery conduits 218A, 218B.

In some configurations, one of the gases inlets 208A, 208B may couple directly with the gases conduit 110 (or indirectly via the complementary connector 118 and/or the gases conduit connector 222). In some such configurations, the bodies 206A, 206B may be integrally formed with or be in the form of a single continuous piece together with the gases conduit 110. In some configurations, one or more of the gases delivery conduits 218A, 218B are removably coupled to one or more of the gases inlets 208A, 208B. In some configurations one or more of the gases delivery conduits 218A, 218B are removably coupled to the gases conduit connector 222.

The bodies 206A, 206B of the patient interface 200 may rest on the patient's face in use. In the illustrated configuration, the bodies 206A, 206B rest on opposing cheeks of the patient's face. To fix the bodies 206A, 206B in place on the patient's face, the bodies 206A, 206B are provided with attachment structures 216A, 216B. The attachment structures 216A, 216B maintain the patient interface 200 in a desired alignment with the patient's face, such that the nasal delivery elements 202A, 202B may, in a non-limiting example, be comfortably and non-sealingly positioned in the patient's nares.

The attachment structures 216A, 216B can couple with fixation structures attached to the face. In some configurations, the attachment structures 216A, 216B and the fixation structures are complementary to one another. The attachment structures 216A, 216B and the fixation structures may couple, for example, via a 'hook-and-loop' style connection, such that the attachment structures 216A, 216B include 'loop' portions (constructed from, for example, textiles or plastics) that couple with complementary 'hook' portions of the fixation structures. Other configurations are contemplated. In some configurations, the attachment structures 216A, 216B may join directly with the patient's face, for example, through the use of adhesive pads or other structures. In some configurations, a single attachment structure may be used. In some configurations, more than two, for example, three or four, attachment structures may be used.

In some configurations, the attachment structures 216A, 216B may include features other than 'loop' portions. For example, the attachment structures 216A, 216B may include 'hook' portions that couple with complementary 'loop' portions on the fixation structures. As another example, the attachment structures 216A, 216B may include snap-fit features or other mechanical interlock features that couple with complementary features on the fixation structures. In some configurations, the headgear 20 may retain the patient interface 200 in a desired orientation or alignment on the face. The headgear 20 may include, for example, one or more straps that extend around the patient's head in use, buckles to adjust the tightness of the straps by modifying the effective length of the straps, caps, coifs, hats, helmets, and/or one or more other features.

A bridge 204 connects the bodies 206A, 206B. The bridge 204 helps to keep the nasal delivery elements 202A, 202B in desired orientations with respect to one another. In some configurations, the bridge 204 is an extension of, and constructed from the same materials as, the bodies 206A, 206B. In some configurations, the bridge 204 is constructed from a different material to the bodies 206A, 206B. In some configurations, the bridge 204 has no internal gases lumen. In some configurations, the bridge 204 may be open to the transmission of gases between the bodies 206A, 206B, for example, via an internal gases lumen that fluidly couples the nasal delivery elements 202A, 202B. In some such configurations, only one of the bodies 206A, 206B has an internal gases lumen and/or gases inlet. In some configurations, the bridge 204 extends between a first connection point on the body 206A and a second connection point on the body 206B.

As shown in FIG. 3, the bodies 206A, 206B may decrease in width (in direction W) as they extend towards the nasal delivery elements 202A, 202B and the bridge 204. The attachment structures 216A, 216B are positioned on relatively wide portions of the bodies 206A, 206B at or near the outer edges of the bodies 206A, 206B to improve stability of the patient interface 200 on the patient's face when the attachment structures 216A, 216B are used together with the fixation structures. For example, the attachment structures 216A, 216B can be positioned at or near a distal portion of the bodies 206A, 206B relative to the nasal delivery elements 202A, 202B. The attachment structures 216A, 216B may substantially cover patient-facing regions of the bodies 206A, 206B, which are regions of the bodies 206A, 206B that face toward the patient's face and away from the patient interface in use. The attachment structures 216A, 216B may at least partially cover the patient-facing regions of the bodies 206A, 206B. The attachment structures 216A, 216B can be positioned within at least partially recessed regions of the bodies 206A, 206B.

With further reference to FIGS. 2 and 4, outer edges of the bodies 206A, 206B can include detachment structures 212A, 212B. The detachment structures 212A, 212B are positioned on interface-facing regions of the bodies 206A, 206B, which are regions of the bodies 206A, 206B that face toward the patient interface and away from the patient's face in use. The detachment structures 212A, 212B are spaced apart from the gases inlets 208A, 208B. In the illustrated configuration, the detachment structures 212A, 212B are tabs that include inner regions of reduced thickness 213A, 213B relative to adjacent portions of the bodies 206A, 206B. Outside of the inner regions of reduced thickness 213A, 213B and towards the outer edge of the bodies 206A, 206B, the detachment structures 212A, 212B include outer regions of normal thickness or increased thickness 215A, 215B relative to adjacent portions of the bodies 206A, 206B.

The detachment structures 212A, 212B are configured such that the outer regions 215A, 215B may be grasped by the patient or another person (for example, a healthcare professional such as but not limited to a nurse or physician) and pulled. When pulled, sufficient force may be exerted on the patient interface 200 that the attachment structures 216A, 216B are detached from the fixation structures attached to the patient's face. The detachment structures 212A, 212B thus may be used to more easily detach the patient interface 200 from the patient's face. Other configurations are contemplated. For example, in some configurations, one detachment structure may be positioned on a single one of the bodies 206A, 206B of the patient interface 200. In some configurations, the patient interface 200 may include more than two, for example, three or four, detachment structures. In some configurations, the detachment structures 212A, 212B may be positioned on other portions of the bodies 206A, 206B, or on other portions of the patient interface 200. In some configurations, the detachment structures 212A, 212B may include structures other than tabs. For example, the detachment structures 212A, 212B may include flat extensions of the bodies 206A, 206B that can be pulled or otherwise manipulated to detach the patient interface 200 from the patient's face.

FIGS. 5A-5D illustrate example embodiments of a fixation structure 300. The fixation structure 300 can have a patient-facing region that joins with the patient's face. FIG. 5A illustrates an example of a patient-facing region of the fixation structure 300. In some embodiments, the fixation structure 300 has an interface-facing region that attaches to the patient interface 200. FIG. 5C illustrates an example of an interface-facing region of the fixation structure 300. In some configurations, the patient-facing region is on a first side of the fixation structure 300 and the interface-facing region is on an opposing second side of the fixation structure 300. As described in more detail below, portions of the fixation structure 300 can be folded and/or flipped. This can result in portions of the first side of the fixation structure 300 changing from facing the patient to facing the interface and portions of the second side of the fixation structure 300 changing from facing the interface to facing the patient.

As indicated above, the fixation structure 300 can attach to the patient interface 200. For example, the fixation structure 300 can releasably attach to the attachment structures 216A, 216B to secure the patient interface 200 to the patient's face. In certain embodiments, the fixation structure 300 can secure a tube, such as a nasogastric, nasojejunal, orogastric, or orojejunal tube, to the patient's face without the need for adhesive tape.

In the illustrated configuration, the fixation structure 300 includes a body 302. The body 302 is of substantially uniform thickness T. In some configurations, the body 302 may be of variable thickness along the length L and/or width W of the body 302. The body 302 may be constructed from a material that can releasably join the patient-facing region of the fixation structure 300 to the patient's face. In the illustrated configuration, the material is an adhesive material, for example a hydrocolloid-based adhesive material, a zinc oxide-based adhesive material, a silicone-based adhesive material, or a hydrogel-based material. As illustrated in FIG. 5B, the patient-facing region of the fixation structure 300 that joins with the patient's face can be covered with a first backing layer 314 that protects the adhesive nature of the body 302. The first backing layer 314 can be removed from the body 302 to expose the adhesive material of the body 302 just prior to use of the fixation structure 300 on the patient's face.

The body 302 includes a first edge 304 that faces towards the patient's nose and/or mouth in use. In the illustrated configuration, the first edge 304 is substantially rounded and tapers in width towards an extension or knob of the body 302. The body 302 includes a second edge 306 that faces away from the patient's nose or mouth in use. In the illustrated configuration, the second edge 306 is substantially rounded and slightly tapers in width. Opposing third and fourth edges 308A, 308B of the body 302 extend between the first and second edges 304, 306. The third and/or fourth edges 308A, 308B may be curved.

The interface-facing region of the fixation structure 300 includes a fixation element 310. The fixation element 310 can engage with the attachment structures 216A, 216B to secure the patient interface 200 to the patient's face. In the illustrated configuration, the fixation element 310 includes a hooked pad to releasably attach to looped pads of the attachment structures 216A, 216B to form a hook-and-loop style connection. The hooked pad may be attached to the fixation structure 300 by, for example, adhesives, ultrasonic welding, high frequency welding, stitching, or chemical bonding. In other configurations, the fixation element 310 may include other structures or elements that can couple with the attachment structures 216A, 216B, including, but not limited to, catches that may couple with complementary latches of the attachment structures 216A, 216B, latches that couple with complementary catches of the attachment structures 216A, 216B, complementary adhesives, pins, clasps, or other mechanical fasteners. In some variants, the fixation element 310 includes a looped pad to releasably attach to hooked pads of the attachment structures 216A, 216B to form a hook-and-loop style connection.

FIG. 5D illustrates an example embodiment of the fixation structure 300. In the illustrated configuration, the fixation element 310 includes a hooked pad with a serpentine shape. The serpentine shape defines gaps 312 between adjacent masses of the fixation element 310. The gaps 312 improve the flexibility of the fixation element 310. In some configurations, the gaps 312 improve the flexibility of the fixation element 310 when the fixation structure 300 is placed under torsion around an axis substantially parallel to the first and/or second edges 304, 306. In some configurations, the gaps 312 could be cuts, slits, fenestrations, or thin regions formed in the fixation element 310. The orientations of the gaps 312 could be varied to suit differing directions of torsion and/or force application.

In some configurations, the fixation element 310 can exhibit increased flexibility under torsion around an axis substantially parallel to the first and/or second edges 304, 306. For example, in some configurations, the fixation element 310 could be constructed from a mechanically anisotropic material that exhibits increased flexibility when under torsion around an axis substantially parallel to the first and/or second edges 304, 306. In still other configurations, the fixation element 310 could be constructed from multiple materials of varying flexibility. The multiple materials could be stratified along a length of the fixation element 310.

Figure 6A:
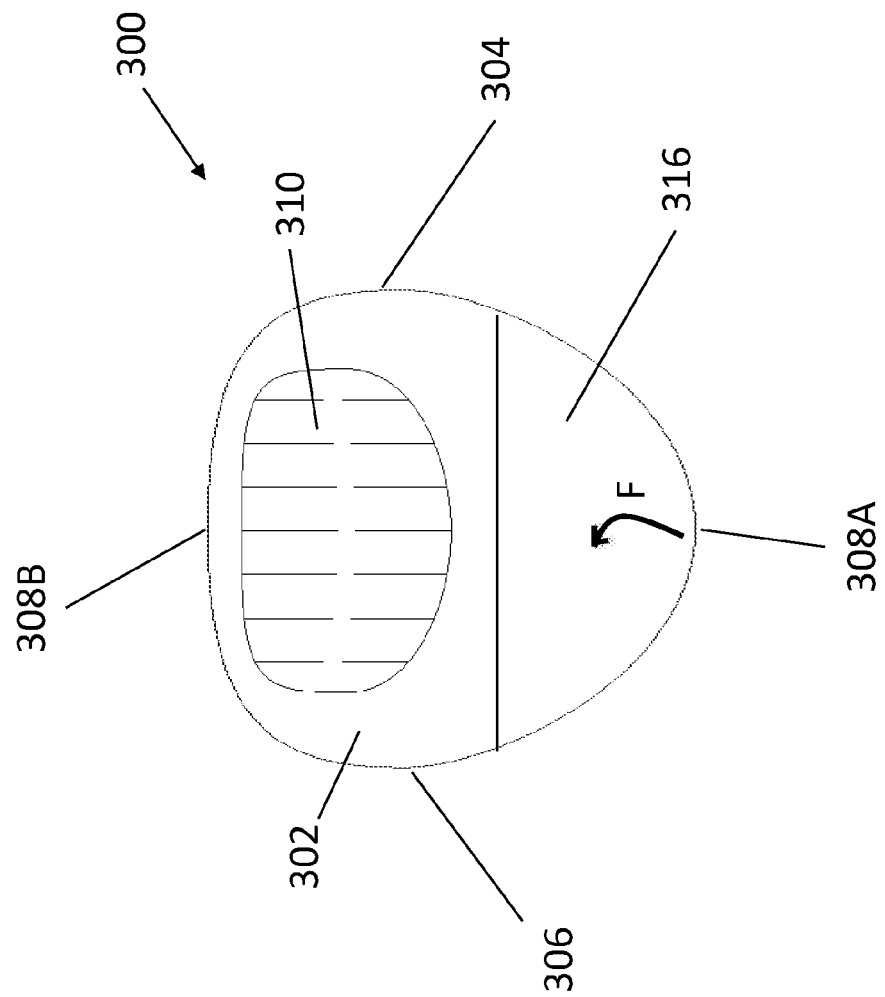

FIGS. 6A-6C illustrate example embodiments of a fixation structure. FIG. 6A illustrates an example configuration of the interface-facing region of the fixation structure 300. In the illustrated configuration, the fixation structure 300 has a triangular shape, or a shape substantially similar to a Reuleaux triangle-like shape, with rounded edges or a 'guitar pick'-like shape. The shape can be substantially symmetrical. The symmetrical shape allows for the fixation structure 300 to be located on either side of the nose and mouth while retaining the same mechanical characteristics, without requiring rotation or re-orientation.

In the illustrated configuration, the fixation element 310 may include a slit pattern, wherein slits extend from outer width-wise edges of the fixation element 310 inwardly towards a center of the fixation element 310. The illustrated slits do not extend across the entirety of the fixation element 310.

With further reference to FIG. 6A, the fixation element 310 is positioned on a first portion of the interface-facing region of the fixation structure 300. A second backing layer 316 is positioned on a second portion of the interface-facing region of the fixation structure 300. The second backing layer 316 can be bounded by the third edge 308A as shown in the illustrated configuration. The second backing layer 316 may be removed by exertion of a force F on the second backing layer 316, causing it to peel off the interface-facing region of the fixation structure 300. In some configurations, the second backing layer 316 may extend beyond one or more edges of the body 302 of the fixation structure 300 to facilitate grasping of the second backing layer 316 by the patient or a user, such as a nurse or other healthcare provider.

As illustrated in FIG. 6B, after the second backing layer 316 is removed from the body 302, a tube 400 can be positioned over the second portion of the interface-facing region of the fixation structure 300. The tube 400 could include one or more of a number of tubes, including, but not limited to, feeding tubes such as nasogastric, orogastric, nasojejunal, or orojejunal tubes, medication delivery tubes, or sensing or measurement tubes (for determination of various parameters including but not limited to gases pressure or gases concentration). The second portion of the interface-facing region of the fixation structure 300 may be folded upon itself and adhered to itself, to the first portion of the interface-facing region of the fixation structure 300, and/or to the tube 400 to secure the tube 400 to the fixation structure 300.

In some configurations, a tube retainment adhesive may be located on the second portion of the interface-facing region of the fixation structure 300 under the second backing layer 316. The tube retainment adhesive may have adhesive properties that are different to the adhesive material used for, or on the body 302. For example, in some configurations, the tube retainment adhesive may include a first adhesive to retain the tube 400 on the fixation structure 300, and the body 302 may be formed from or include a second adhesive to secure the fixation structure 300 to the face. In some configurations, the first and second adhesives may differ, for example, the tube retainment adhesive might include a hydrocolloid-based adhesive and the body 302 might be formed from or include a silicone-based adhesive. In some configurations, the first and second adhesives may be the same. In some configurations, the first and second adhesives may be from the same class of material.

In some configurations, the tube retainment adhesive includes an adhesive that is less adhesive that the adhesive of the body 302. For example, the tube retainment adhesive may have an adhesive strength that is relatively low, and the body 302 may be formed from or include an adhesive with an adhesive strength that is relatively high. Configuring the adhesives in such a manner can be useful if it is desired to remove or adjust the tube 400 without inadvertently removing or adjusting a patient interface used with the fixation structure 300.

Figure 7A:
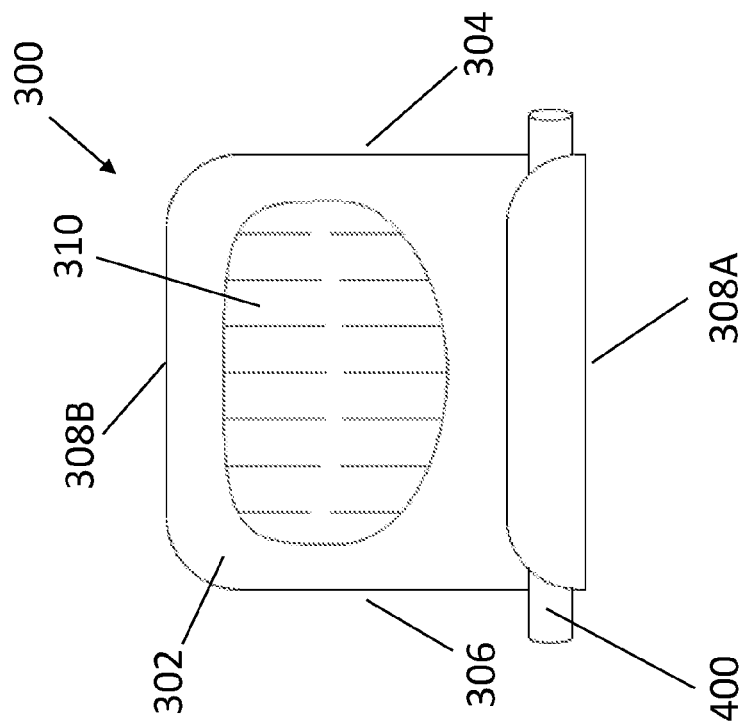
FIGS. 7A-7B illustrate example embodiments of a fixation structure.
Figure 7B:
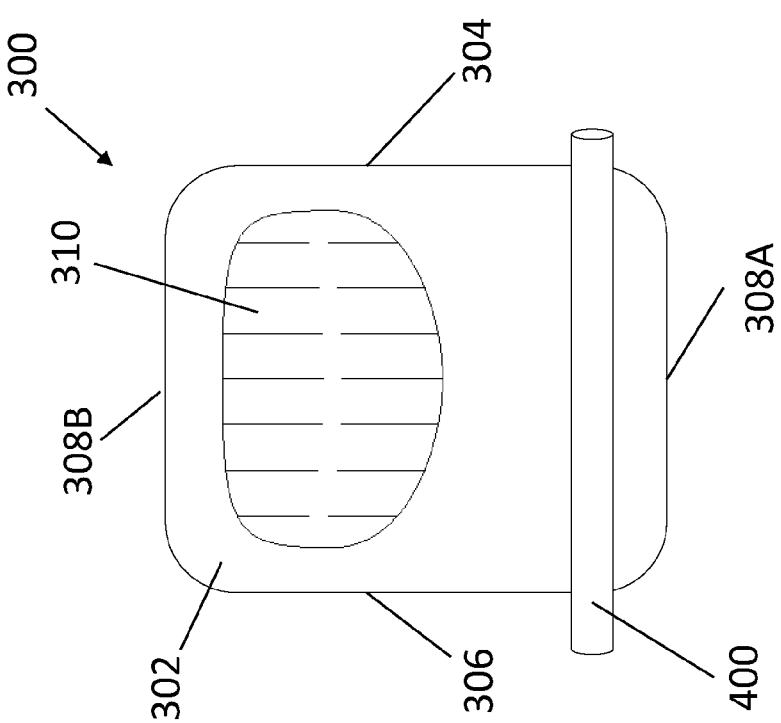

Although FIGS. 6A-6C illustrate that the fixation structure 300 with a triangular shape, or a shape substantially similar to a Reuleaux triangle-like shape, with rounded edges or a 'guitar pick'-like shape may secure the tube 400, in other configurations other shapes for the fixation structure 300 may be used. For example, FIGS. 7A-7B illustrate that the fixation structure 300 can have a rectangle-like shape. Still other shapes, including but not limited to, square, rectangular, triangular, circular or hexagonal shapes, are contemplated. In some configurations, modifications to the shapes, such as rounded edges, curvature, or slight tapering may be contemplated.

Figure 8A:
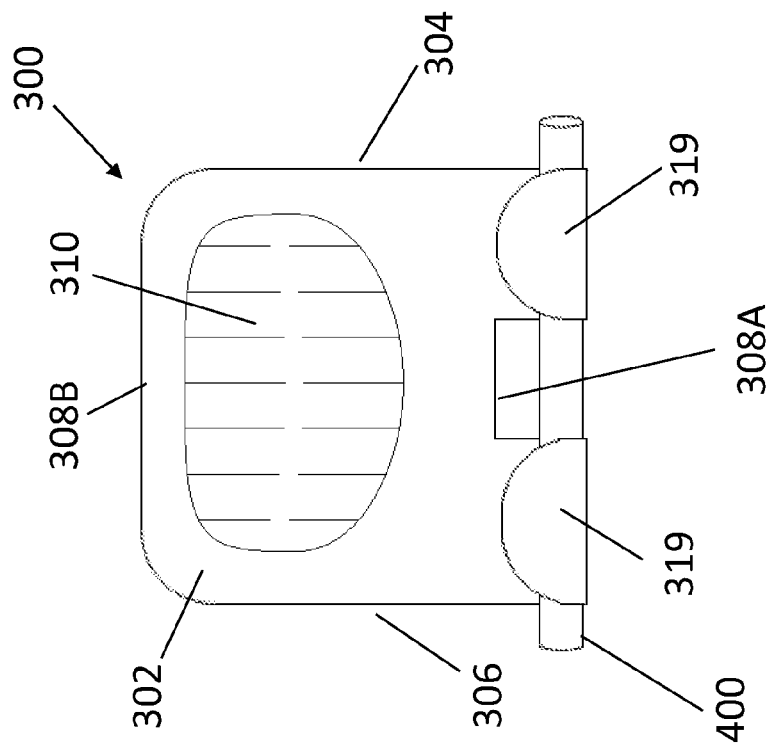
Figure 8B:
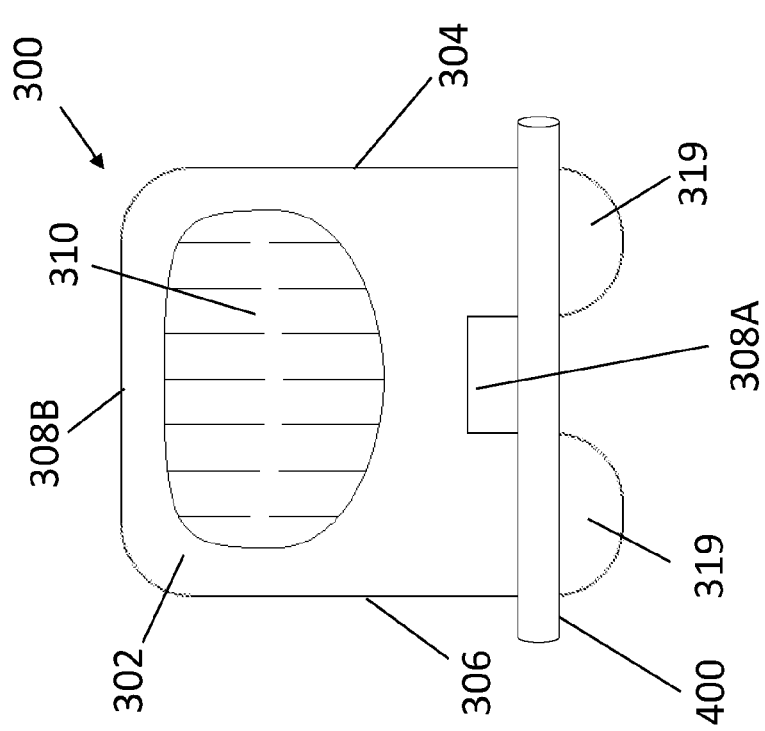

FIGS. 8A-8B illustrate an example shape for the fixation structure 300 to secure the tube 400. In the illustrated configuration, the second portion of the interface-facing region of the fixation structure 300 includes one or more legs 319 that extend outwardly from the body 302. In the illustrated embodiment, two legs 319 are shown. In some embodiments, there may be more than two legs 319. The legs 319 are substantially parallel to one another and are on opposing sides of the third edge 308A of the body 302; for example, one of the legs 319 is positioned near the first edge 304, and the other of the legs 319 is positioned near the second edge 306. Some or all of the legs 319 may include adhesives that allow the legs 319 to be folded back upon the body 302 to secure the tube 400. The tube 400 may be positioned at the folded portion between the legs 319 and the body 302, on the legs 319 (as shown), or on the body 302 and thus held in place by the legs 319. In some embodiments, upon folding, the legs 319 extend into the body 302. The adhesives on the legs 319 may be covered by one or more backing layers (for example, the second backing layer 316). The positioning of the legs 319 on the third edge 308A may evenly support the tube 400, while allowing for numbers or other markings present on the tube 400 to be read in a gap between the legs 319.

In other configurations, as illustrated in FIG. 8C, the legs 319 are offset from one another at an angle x. In some embodiments, the angle x is less than about 180 degrees, or less than about 60 degrees, or between about 60 degrees to about 180 degrees. FIG. 8D illustrates the legs 319 folded to hold the tube 400 and adhered to the body 302. In the folded position, the legs 319 extend beside the fixation element 310. The fixation element 310 is configured such that it is not obscured or covered by the legs 319. The tube 400 is positioned at the folded portion between the legs 319 and the body 302. Alternatively, the tube 400 can be positioned on the body 302 between the folded portion and the fixation element 310.

Figure 9B:
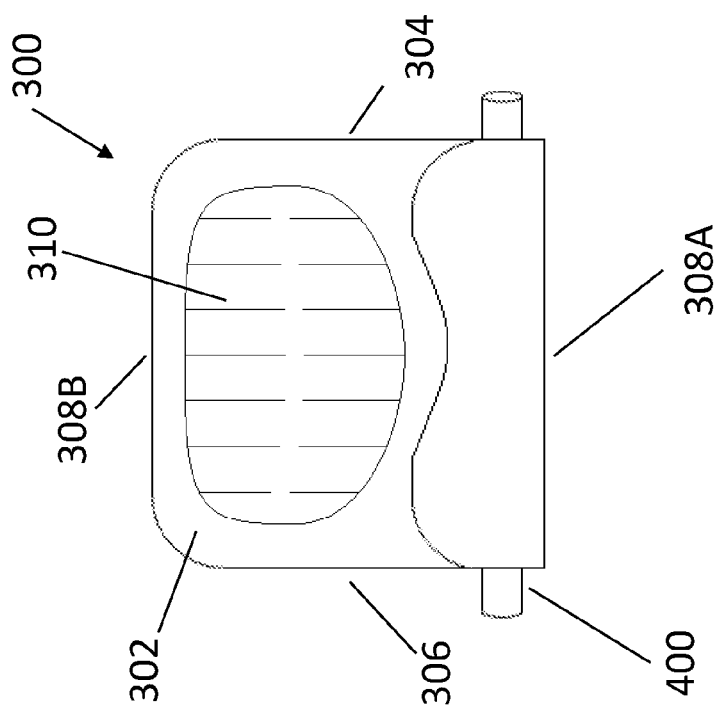
FIGS. 9A-9B illustrate example embodiments of a fixation structure.
Figure 9A:
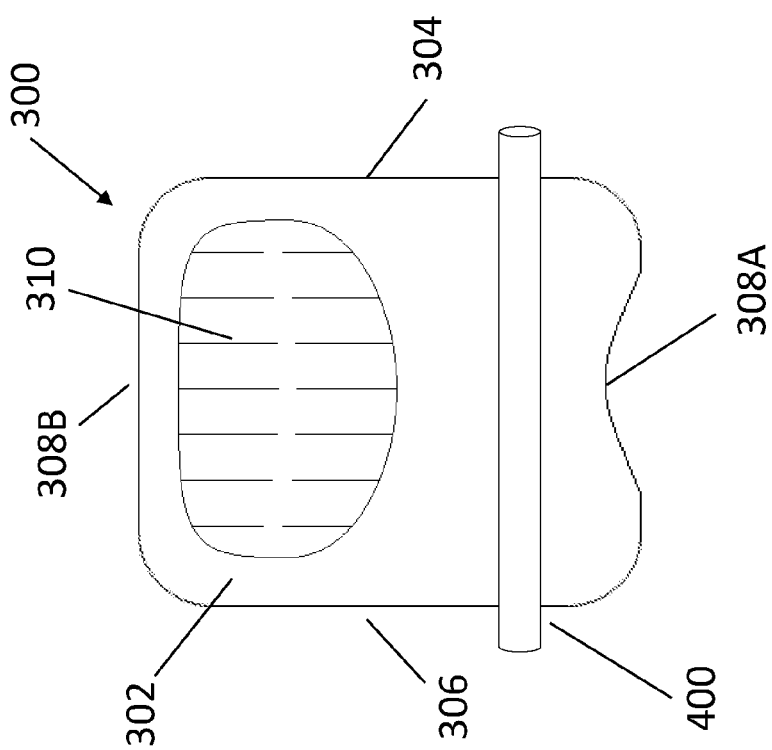

FIGS. 9A-9B illustrate an example shape for the fixation structure 300 to secure the tube 400. In the illustrated configuration, the second portion of the interface-facing region of the fixation structure 300 includes a recess or cutout along the third edge 308A of the body 302. The cutout is substantially contoured and is substantially complementary to an edge of the fixation element 310 (in the illustrated configuration, the edge facing the third edge 308A of the body 302) when folded over the tube 400. The cutout maximizes the exposed area of the fixation element 310 by not obscuring or covering the fixation element 310, without increasing the size of the fixation structure 300. If the cutout is complementary to the edge of the fixation element 310, an aesthetically appealing and ergonomic shape can be realized.

FIGS. 10A-10C illustrate an example configuration for the fixation structure 300 to secure the tube 400. In the illustrated configuration, part of the body 302 may be bifurcated so as to provide an encapsulation for the tube 400. As illustrated in FIG. 10B, the body 302 is bifurcated around a central portion of the body 302 creating a bifurcation joint J. Upper and lower body portions $302_u$, $302_l$ extend from the bifurcation joint J towards the third edge 308A of the body 302. Inner portions of the upper and lower body portions $302_u$, $302_l$ are covered with upper and lower second backing layers 318A, 318B, under which are located upper and lower adhesives, respectively. Similarly to the tube retainment adhesive described elsewhere in this disclosure with reference to FIGS. 6A-6C, the upper and lower adhesives may have adhesive properties or adhesive strengths different to adhesive properties or adhesive strength of the adhesive material used for or on the body 302. In some configurations, the upper and lower adhesives may have adhesive properties or adhesive strengths that are the same or similar to the adhesive properties and/or strength of the adhesive material used for on the body 302. To utilize the illustrated fixation structure 300, the first backing layer 314 can be removed to expose an adhesive surface that may be adhered to the face. After removal of the upper and lower second backing layers 318A, 318B, the tube 400 can be positioned under the upper body portion $302_u$ and over the lower body portion $302_l$ such that it is secured between the upper and lower body portions $302_u$, $302_l$. In some configurations, the fixation structure 300 can include other shapes, including, but not limited to, a rectangle-like shape with/without rounded edges as described elsewhere in this disclosure with reference to FIGS. 7A-7B.

Figure 11B:
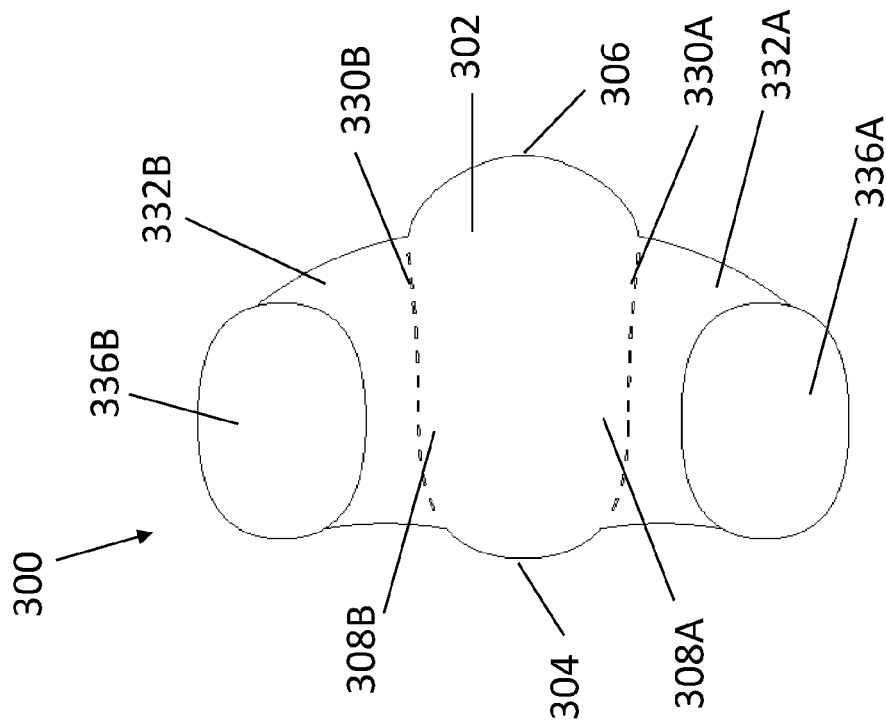
FIGS. 11A-11B illustrate example embodiments of a fixation structure.
Figure 11A:
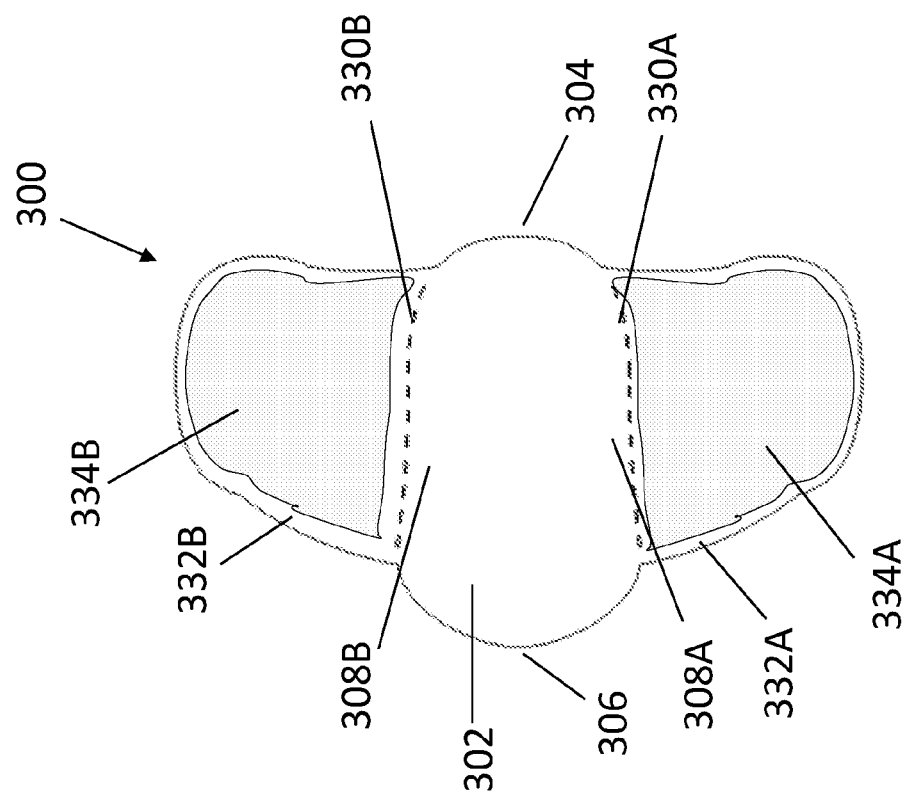

FIGS. 11A-11B illustrate an example configuration for the fixation structure 300 to secure the tube 400. The illustrated fixation structure 300 includes the body 302. FIG. 11A illustrates the interface-facing region of the body 302, and FIG. 11B illustrates the patient facing region of the body 302. The body 302 is formed from or includes an adhesive material to adhere to the patient's face in use. In the illustrated configuration, the body 302 is formed from or includes a hydrocolloid-based adhesive material. The body 302 includes the first edge 304 that faces towards the nose or mouth of a patient in use and the second edge 306 that faces away from the patient's nose or mouth in use. The opposed third and fourth edges 308A, 308B extend between the first and second edges 304, 306. As illustrated, in some configurations, the third and fourth edges 308A, 308B are curved. In some configurations, the curves are at least partially concave with respect to the third and fourth edges 308A, 308B. The curves can substantially correspond with a contour of an eye or an eyelid. When forces are exerted on the body 302 of the fixation structure 300 that would urge the body 302 towards the eye or eyelid, the curvature increases the tendency of the body 302 to cup or move around the contour of the lower eyelid and decreases the tendency of the body 302 to move into or near the eye or eyelid.

The third and fourth edges 308A, 308B may project farther from a centerline or center portion of the body 302 at parts of the third and fourth edges 308A, 308B that are proximal to the first and second edges 304, 306 than the third and fourth edges 308A, 30B project from the centerline or center portion of the body 302 at parts of the third and fourth edges 308A, 308B that are distal from the first and second edges 304, 306 (for example, central portions of the third and fourth edges 308A, 308B). In some configurations, portions of the third and fourth edges 308A, 308B proximal to the second edge 306 may project farther from the centerline or center portion of the body 302 than do portions of the third and fourth edges 308A, 308B proximal to the first edge 304.

The body 302 includes a pair of separable extensions 332A, 332B. In the illustrated configuration, the separable extensions 332A, 332B are formed from the same material as the body 302. In some configurations, the separable extensions 332A, 332B are formed from a different material than the body 302. The separable extensions 332A, 332B may be substantially wing-shaped. The separable extensions 332A, 332B are at least partially linked to the body 302 at the third and fourth edges 308A, 308B of the body 302 and may project outwardly from the body 302. The separable extensions 332A, 332B are linked to the body 302 by perforated sections 330A, 330B. The perforated sections 330A, 330B can be torn to allow the separable extensions 332A, 332B to be separated from the body 302. In some configurations, one of the perforated sections 330A, 330B can link the body 302 with the separable extensions 332A, 332B. In some configurations, multiple perforated sections 330A, 330B (for example, two, three, or four perforated sections) can link the body 302 with the separable extensions 332A, 332B.

The separable extensions 332A, 332B retain or encapsulate the tube 400. As shown in FIG. 11A, on the sides of the separable extensions 332A, 332B corresponding to the interface-facing region of the body 302, the separable extensions 332A, 332B include adhesive layers 334A, 334B to retain the tube 400. The adhesive layers 334A, 334B may be formed from or include adhesives that are appropriate for adhering to plastic feeding tubes, including, but not limited to, hydrocolloid-based adhesives and acrylic-based adhesives. One or more of the adhesive layers 334A, 334B may be covered by backing layers to protect the adhesive nature of the adhesive layers 334A, 334B.

In some embodiments, the fixation structure 300 includes adhesive and non-adhesive portions. For example, the interface-facing region of the body 302 can be non-adhesive and the interface-facing region of the separable extensions 332A, 332B can be adhesive, or vice-versa. This can aid in removing the fixation structure 300 from the tube 400, such as by tearing the fixation structure 300 along a row of perforations and separating the fixation structure 300 from the tube 400 via the tear. It has been found that, in some implementations, when both the body 302 and the extensions 332A, 332B are adhesive, the fixation structure 300 can become overly fixed to itself. This can inhibit removing the fixation structure 300 from the tube 400, such as by interfering with the ability to tear along the perforations. However, in some implementations, when only one of the body 302 and the separable extensions 332A, 332B includes an adhesive portion, the adherence of the fixation structure 300 to itself does not overly inhibit removal of the fixation structure 300 from the tube 400.

As shown in FIG. 11B, on the sides of the separable extensions 332A, 332B corresponding to the patient-facing region of the body 302, the separable extensions 332A, 332B include fixation elements 336A, 336B. The fixation elements 336A, 336B each engage with one of the attachment structures 216A, 216B in the same or a similar way as the fixation elements 310 described elsewhere in this disclosure with reference to FIG. 3. In the illustrated configuration, the fixation elements 336A, 336B include 'hook' pads to couple with the attachment structures 216A, 216B for a 'hook-and-loop' style connection. In some embodiments, the fixation structure 300 can adhere to other surfaces, such as the patient's skin, the tube 400, etc. For example, the fixation structure 300 can include one or more adhesive portions and one or more non-adhesive portions. In certain embodiments, one or both of the separable extensions 332A, 332B include adhesive portions.

Figure 12A:
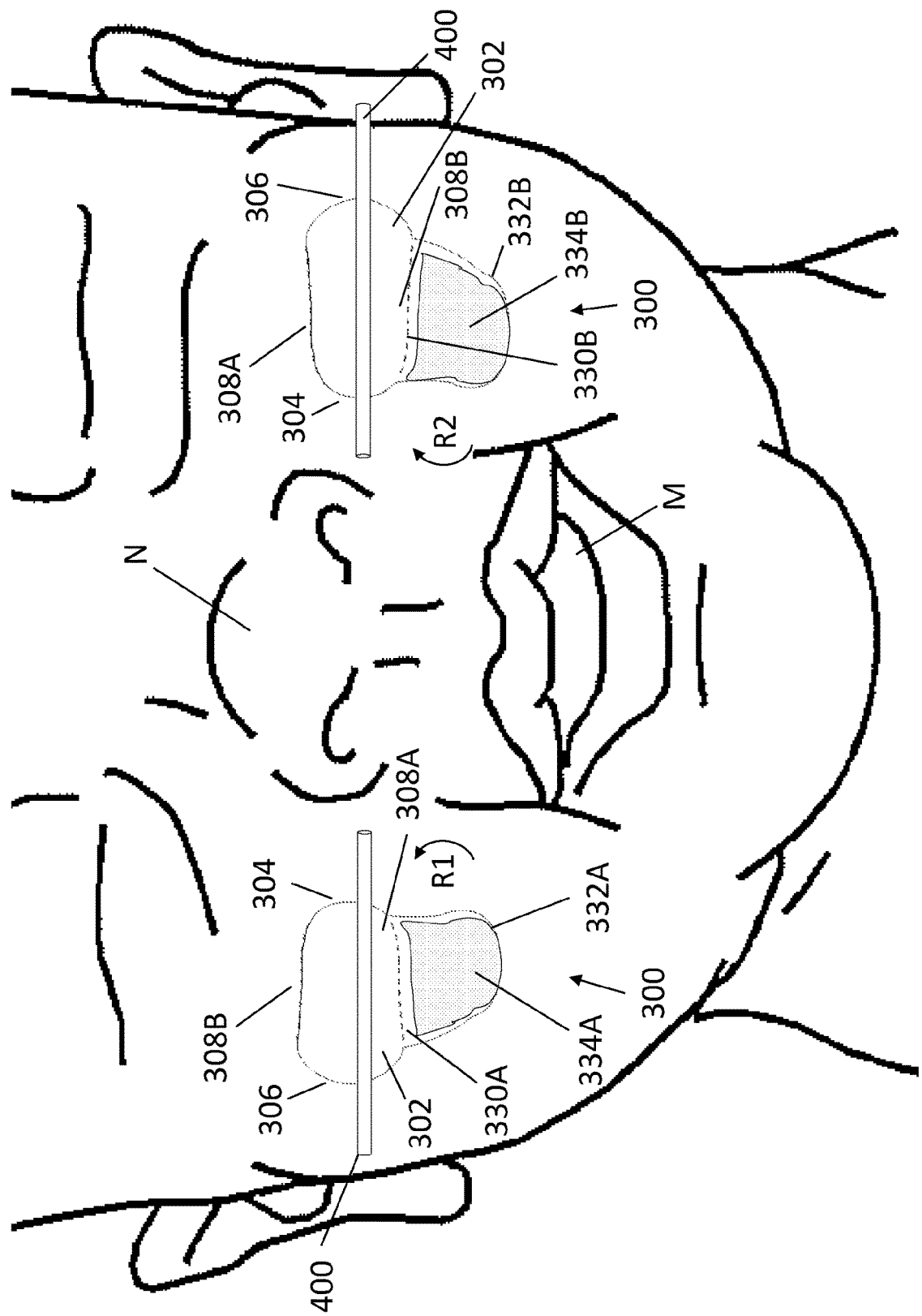
FIGS. 12A-12B illustrate an example use of the fixation structure of FIGS. 11A-11B.
Figure 12B:
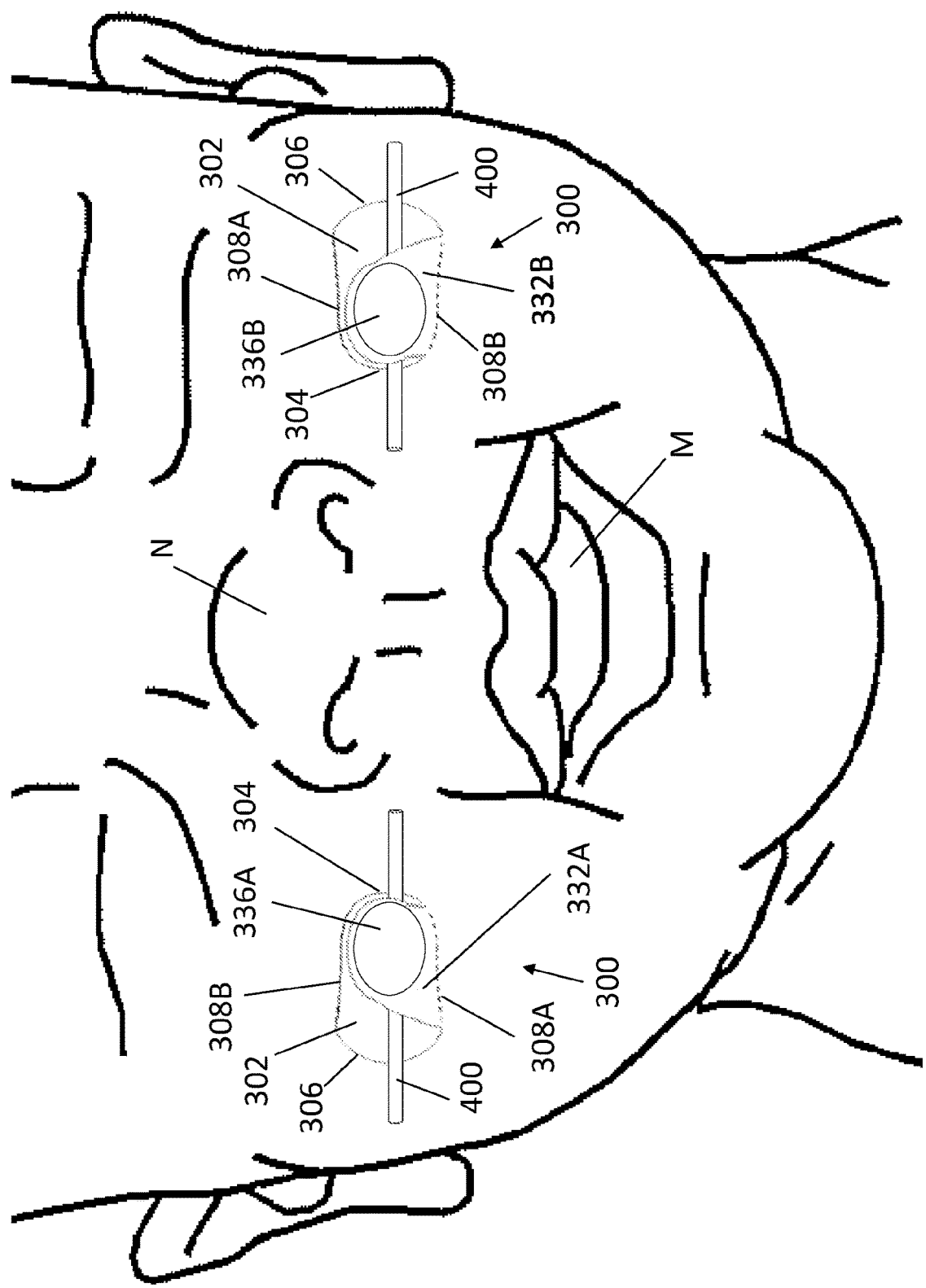
Figure 16A:
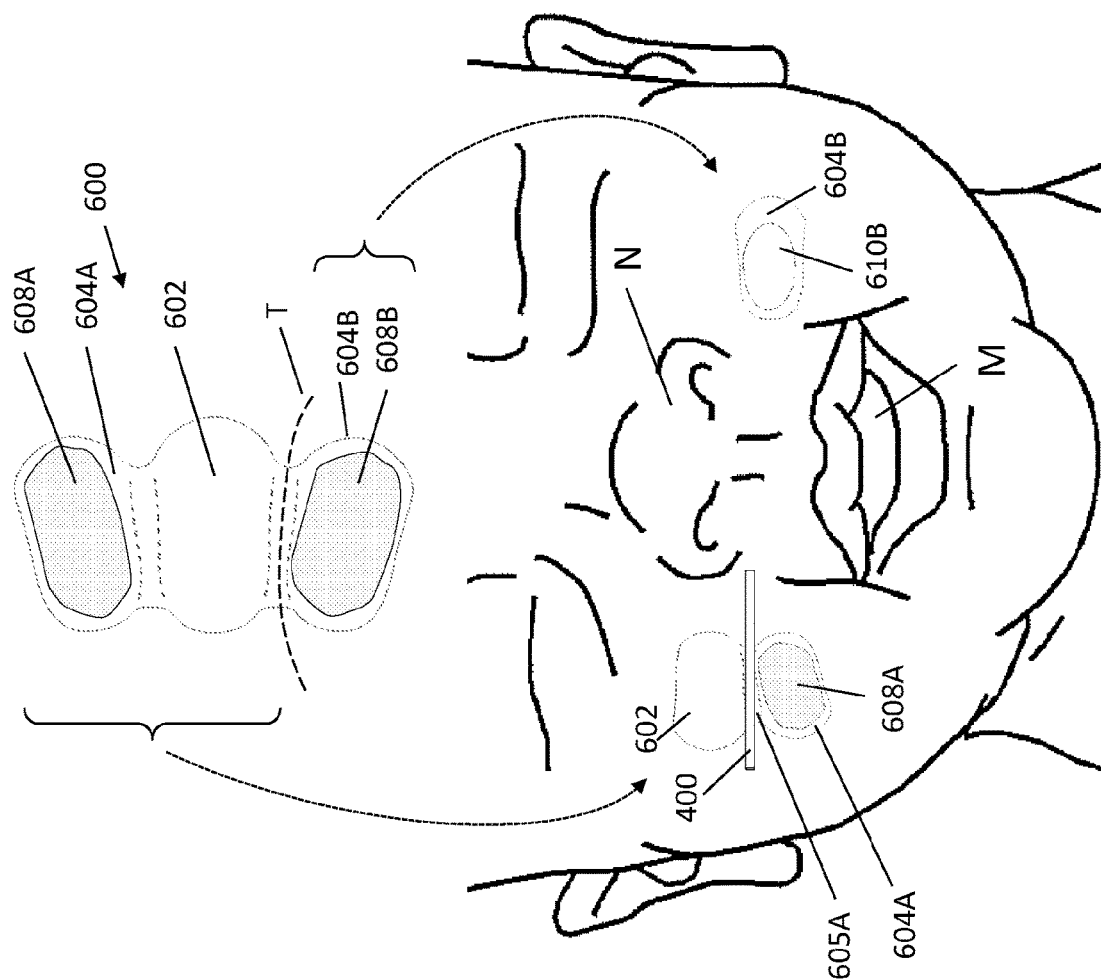
FIGS. 16A-16B illustrate an example use of the fixation structure assembly of FIGS. 15A-15B.
Figure 16B:
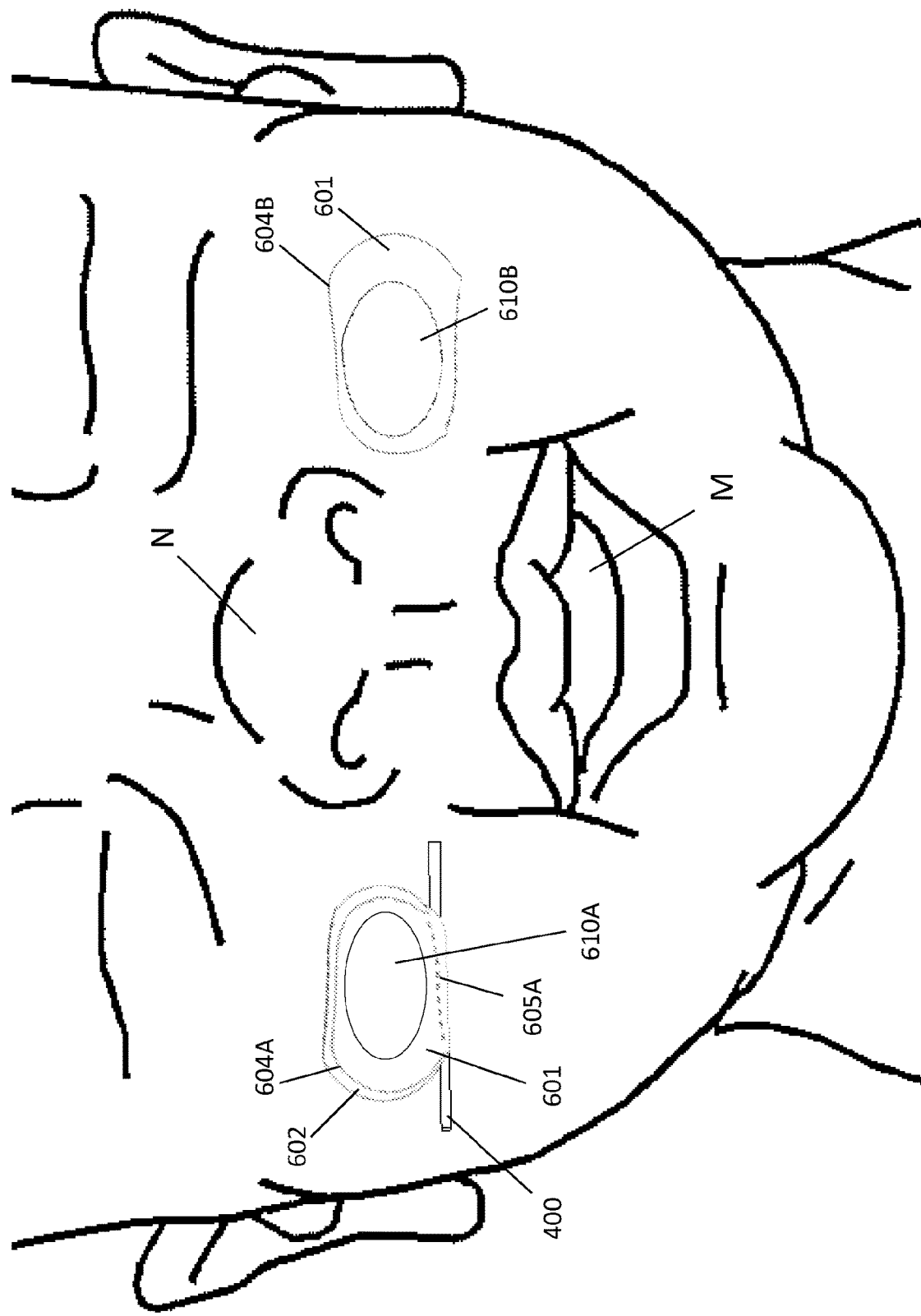

FIGS. 12A and 12B illustrate the use of the fixation structure 300 illustrated in FIGS. 11A and 11B. A close-up of a face of a patient is shown, with a nose N and mouth M. With attention to the left-hand portions of FIG. 12A and FIG. 12B, to use the fixation structure 300, one of the separable extensions 332B can be removed from the body 302 (as illustrated in FIGS. 16A-16B). The body 302 may be adhered to the left side of the face under the nose N and above the mouth M. The tube 400 can then be positioned on the body 302. The backing layer over the adhesive layer 334A present on the remaining separable extension 332A can be removed, exposing the adhesive layer 334A. The tube 400 can be covered and held into place by grasping the separable extension 332A and folding it over the tube 400 in a direction R1. The adhesive layer 334A can be used to secure the tube 400 to the body 302. When folded, the fixation element 336A of the separable extension 332A is exposed, allowing the fixation element 336A to couple with the corresponding attachment structure 216A of the patient interface 200. The separable extension 332A can be positioned such that it is near to the eye prior to folding, or such that it is away from the eye prior to folding.

With attention to the right-hand portions of FIG. 12A and FIG. 12B, the fixation structure 300 (or a second fixation structure) might be rotated by 180 degrees to be used on the other side of the face in a direction R2. In this case, the separable extension 332A may be removed. When folded, the fixation element 336B of the fixation structure 300 is exposed such that it can couple with the corresponding attachment structure 216B of the patient interface 200. The separable extension 332B can be positioned such that it is near to the eye prior to folding, or such that it is away from the eye prior to folding. In some embodiments, the fixation structure 300 is not used to hold the tube 400. In some embodiments, each of multiple fixation structures can hold one or more tubes.

Figure 13B:
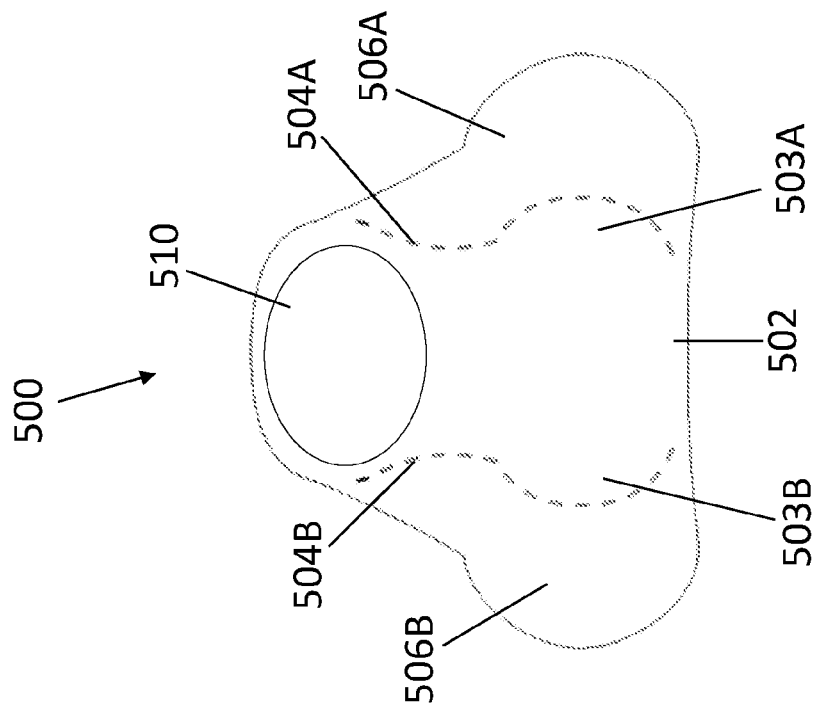
FIGS. 13A-13B illustrate example embodiments of a fixation structure.
Figure 13A:
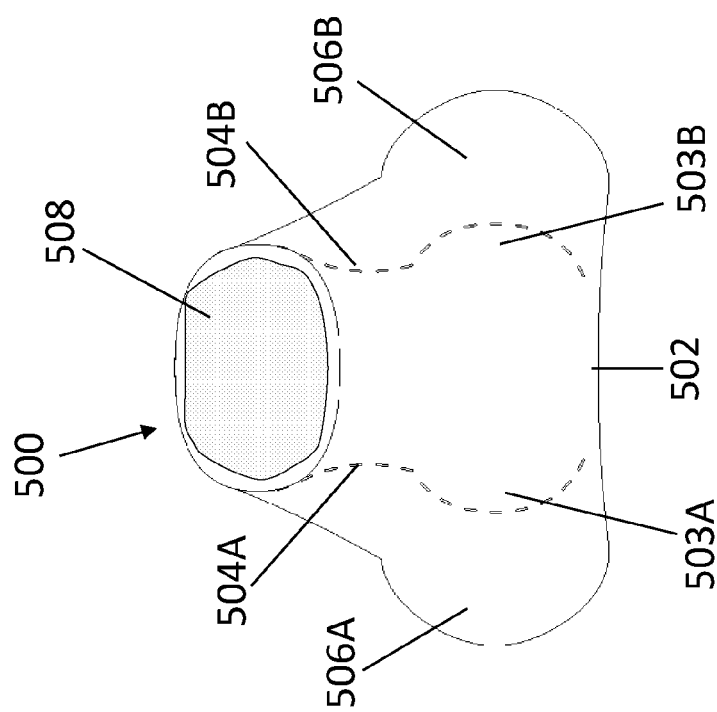

FIGS. 13A-13B illustrate an example configuration for a fixation structure 500 to secure the tube 400. The illustrated fixation structure 500 includes a body 502. FIG. 13A illustrates an interface-facing region of the body 502, and FIG. 13B illustrates a patient-facing region of the body 502. The patient-facing region of the body 502 is formed from or includes an adhesive material to adhere to the patient's face. In the illustrated configuration, the body 502 is formed from or includes a hydrocolloid-based adhesive material. The body 502 includes opposed first and second edges 503A, 503B. Each of the first and second edges 503A, 503B face towards or face away from the patient's nose or mouth in use. The fixation structure 500 can be substantially symmetrical such that rotation of the fixation structure 500 is not required to fit it on either side of the face. As shown in FIG. 13A, the body 502 includes a tube-retaining adhesive 508 on a portion of the interface-facing region of the body 502. In some embodiments, the tube-retaining adhesive 508 can cover the entirety of the folding portion of the fixation structure 500. In some embodiments, the interface-facing region of the body 502 includes at least a portion of an adhesive material. In some embodiments, the entirety of the body 502 includes an adhesive material. The tube-retaining adhesive 508 can adhere to the adhesive material on the body 502 to facilitate coupling therebetween. As shown in FIG. 13B, the body 502 includes a fixation element 510 on a portion of the patient-facing region of the body 502. The fixation element 510 engages with one of the attachment structures 216A, 216B (described elsewhere in this disclosure with reference to FIG. 3). In the illustrated configuration, the fixation element 510 includes a 'hook' pad to couple with one of the attachment structures 216A, 216B for a 'hook-and-loop' style connection.

The body 502 includes a pair of separable extensions 506A, 506B. In the illustrated configuration, the separable extensions 506A, 506B are formed from the same material as the body 502. In some configurations, the separable extensions 506A, 506B can be formed from a different material to the body 502. The separable extensions 506A, 506B are linked to the body 502 at the first and second edges 503A, 503B of the body 502. The separable extensions 506A, 506B are linked to the body 502 by perforated sections 504A, 504B. The perforated sections 504A, 504B can be torn to allow the separable extensions 506A, 506B to be separated from the body 502. In some configurations, a single set of the perforated sections 504A, 504B link the body 502 with the separable extensions 506A, 506B. In some configurations, multiple sets of the perforated sections 504A, 504B (for example, two, three, or four sets) can link the body 502 with the separable extensions 506A, 506B. The separable extensions 506A, 506B retain or encapsulate the tube 400.

Figure 14A:
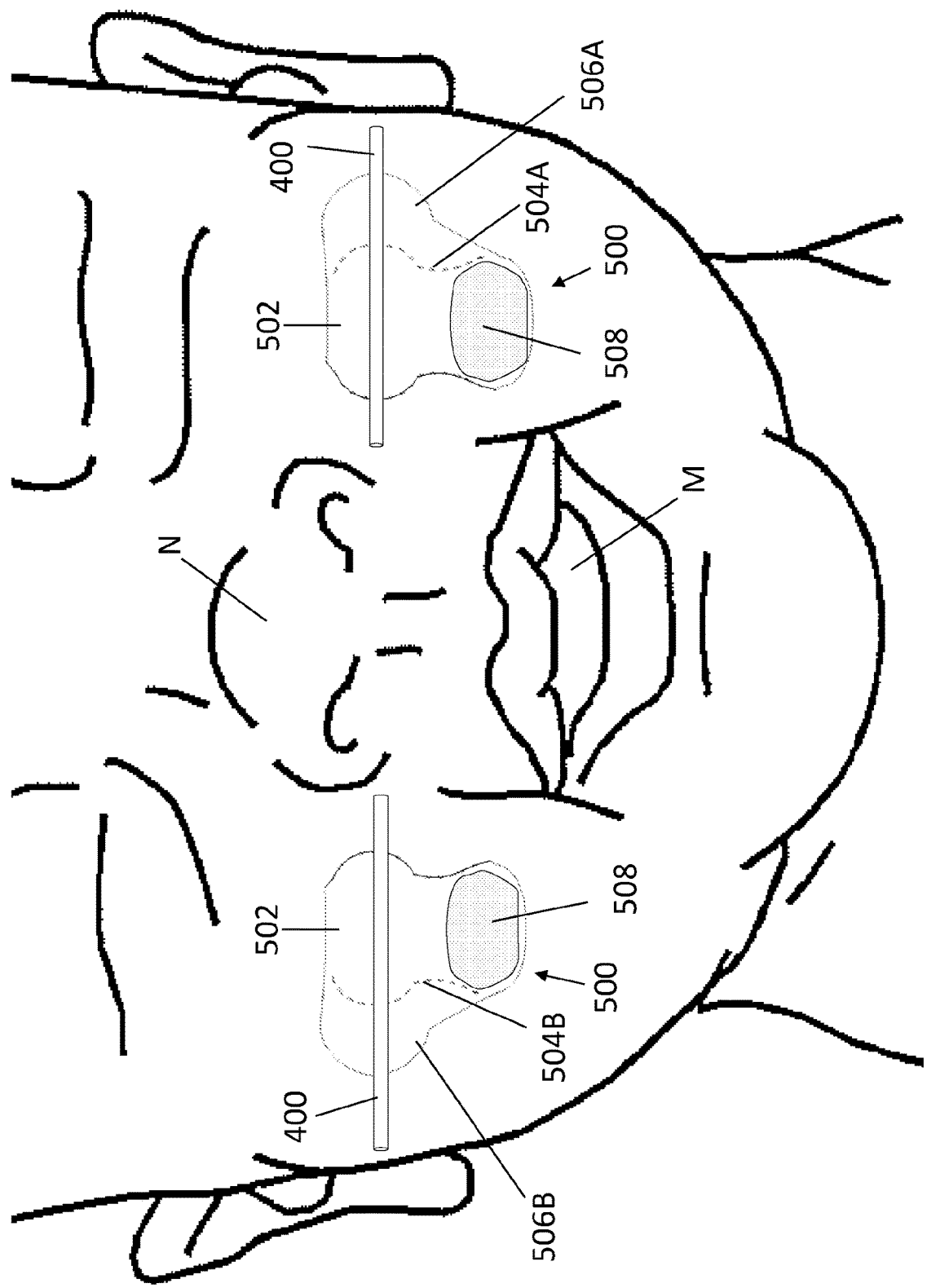
FIGS. 14A-14B illustrate an example use of the fixation structure of FIGS. 13A-13B.
Figure 14B:
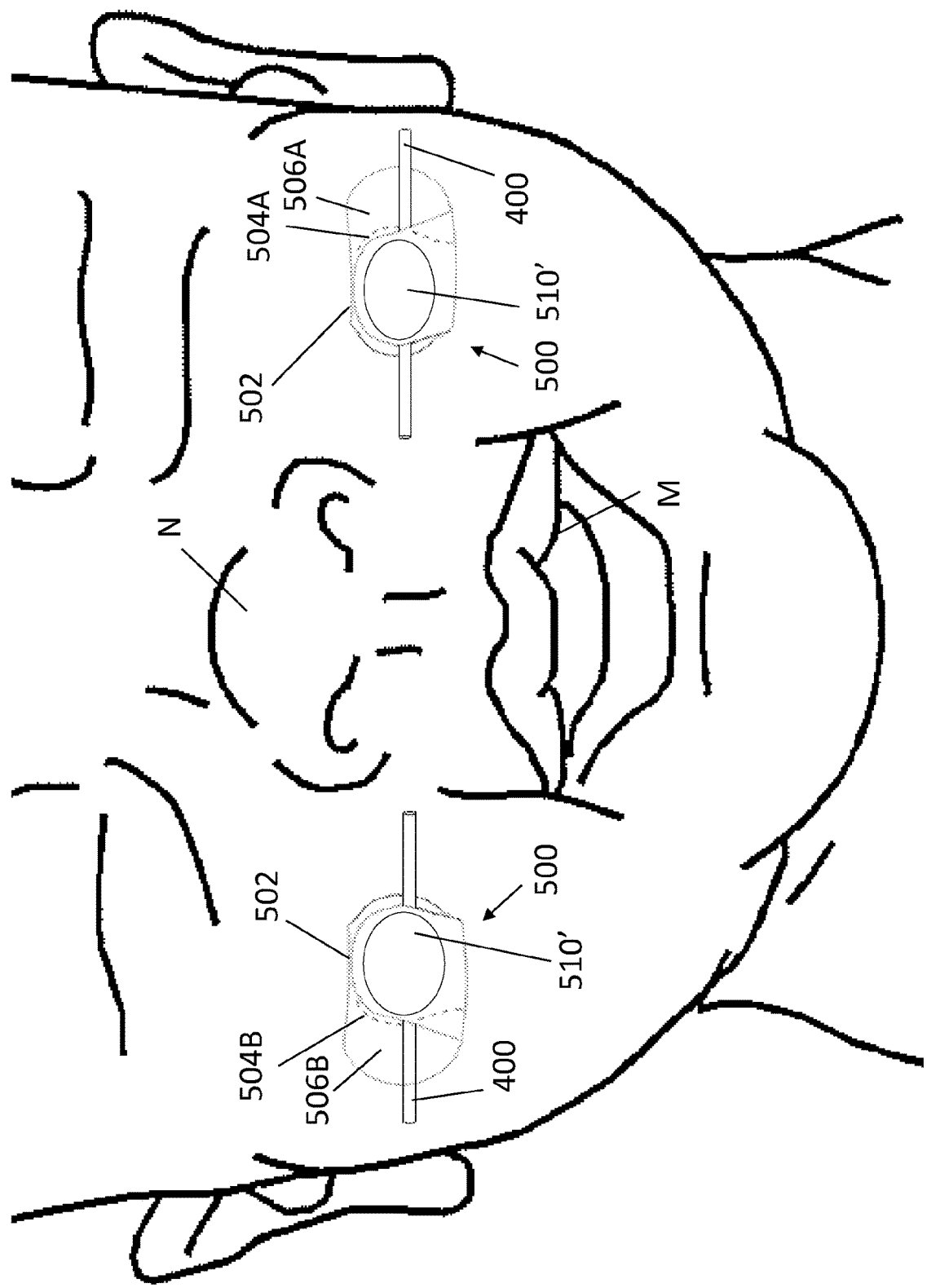

FIGS. 14A and 14B illustrate the use of the fixation structure 500 illustrated in FIGS. 13A and 13B. A close-up of a face of a patient is shown, with a nose N and mouth M. With attention to the left-hand portions of FIGS. 14A and 14B, to use the fixation structure 500, one of the separable extensions 506A can be removed from the body 502. The tube 400 can be placed on the body 502 and the remaining separable extension 506B. The side of the body 502 comprising the tube-retaining adhesive 508 can be folded over the tube 400 together with the remaining separable extension 506B to secure the tube 400 to the body 502. When folded, the fixation element 510 of the body 502 is exposed, allowing the fixation element 510 to couple with one of the attachment structures 216A, 216B of the patient interface 200.

With attention to the right-hand portions of FIG. 14A and FIG. 14B, the fixation structure 500 (or a second fixation structure) might be used on the other side of the face. In this case, the separable extension 506B can be removed. As above, the tube 400 is positioned on the body 502 such that the tube-retaining adhesive 508 can fold over the tube 400 and adhere to the body 502, holding the tube 400 in place. The tube retaining adhesive 508 can be positioned such that it is near the eye prior to folding, or such that it is away from the eye prior to folding. When folded, the fixation element 510 of the fixation structure 500 is exposed such that it can couple with one of the attachment structures 216A, 216B of the patient interface 200. Although the other illustrated fixation structure is used to retain the tube 400, in other configurations, none or multiple of tubes may be used with the other fixation structure.

In the illustrated embodiments, the tube retaining adhesive 508 portion of the fixation structure 500 is positioned away from the patient's eye region to reduce the risk of it loosening and opening onto or near the eye in use, causing discomfort to the patient.

FIGS. 15A and 15B illustrate an example configuration for a fixation structure assembly 600 to secure the tube 400. The fixation structure assembly 600 includes a body 602, first and second intermediate regions 605A, 605B, perforated sections 606A$_1$, 606A$_2$, 606B$_1$, 606B$_2$, and first and second separable extensions 604A, 604B. FIG. 15A illustrates an interface-facing region of the body 602 of the fixation structure assembly 600. FIG. 15B illustrates a patient-facing region of the body 602. The body 602 is formed from or includes an adhesive material to adhere to the patient's face. In the illustrated configuration, the body 602 is formed from or includes a hydrocolloid-based adhesive material. As illustrated in FIG. 15A, the sides of the separable extensions 604A, 604B corresponding to the interface-facing region of the body 602 include adhesive portions 608A, 608B. As illustrated in FIG. 15B, the sides of the separable extensions 604A, 604B corresponding to the patient-facing region of the body 602 include fixation elements 610A, 610B. The fixation elements 610A, 610B engage with the attachment structures 216A, 216B (described elsewhere in this disclosure with reference to FIG. 3) to secure the patient interface 200 to the face. In the illustrated configuration, the fixation elements 610A, 610B include 'hook' pads to couple with the attachment structures 216A, 216B for a 'hook-and-loop' style connection.

Figure 15C:
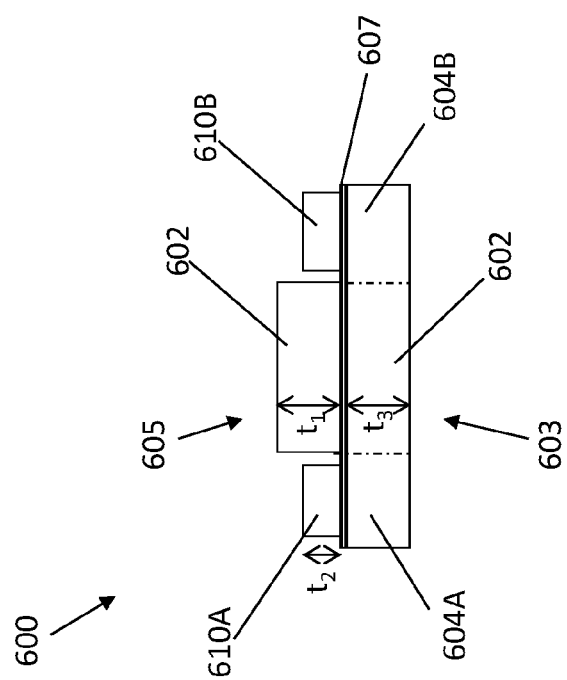
FIG. 15C illustrates a cross-section of the fixation structure assembly of FIG. 15B along the line A-A.

FIG. 15C illustrates a cross-section of the fixation structure assembly of FIG. 15B along the line A-A. As illustrated, the fixation structure assembly 600 includes an interface-facing region 603 and a patient-facing region 605. The interface-facing region 603 includes a portion of the body 602 between the separable extensions 604A, 604B, which are indicated in FIG. 15C via an imaginary dashed line that distinguishes the separable extensions 604A, 604B from the body 602. The separable extensions 604A, 604B can include an adhesive material. The patient-facing region 605 includes the fixation elements 610A, 610B, with a portion of the body 602 therebetween. The patient-facing region 605 includes an adhesive material. The interface-facing region 603 and the patient-facing region 605 can, in some embodiments, be separated by a film 607.

In the illustrated embodiment, the portion of the body 602 in the patient-facing region 605 has a greater thickness $t_1$ than the thickness $t_2$ of the fixation elements 610A, 610B. In some embodiments, the thickness $t_3$ of the portion of the body 602 in the interface-facing region 603 is approximately the same thickness as the thickness $t_1$ of the portion of the body 602 in the patient-facing region 605. The thicknesses $t_1$, $t_2$, and $t_3$ can be varied to suit different materials and/or applications. For example, the thickness $t_2$, may, in some embodiments, be greater than the thickness $t_1$ and/or $t_3$. In some embodiments, the thickness $t_1$ can be different from the thickness $t_3$. In some embodiments, the body 602 of the interface-facing region 603 includes an adhesive material. As previously described, one of the separable extensions 604A, 604B can fold such that the adhesive material couples the one of the separable extensions 604A, 604B to the body 602 of the interface-facing region 603. This causes one of the fixation elements 610A, 610B to be exposed on the interface-facing region 603, such that it can couple with the patient interface 200. The other separable extension can be removed via perforated sections 606B$_1$, 606B$_2$ as described above, and to couple, via the adhesive material, to the patient's face, such that the fixation element is exposed to facilitate coupling between the separable extension and the patient interface 200.

FIGS. 16A and 16B illustrate the use of the fixation structure assembly 600 illustrated in FIGS. 15A and 15B. A close-up of a face of a patient is shown, with a nose N and mouth M. The fixation structure assembly 600 may be torn along tear line T, detaching one of the separable extensions 604B along the perforated sections 606B$_1$ and/or 606B$_2$. In the illustrated embodiment, a pair of perforated sections 606B$_1$, 606B$_2$ links the body 602 with one of the separable extensions 604A, 604B. In some embodiments, only a single one of the perforated sections 606B$_1$ or 606B$_2$ link the body 602 with one of the separable extensions 604A, 604B. In some embodiments, multiple of the perforated sections 606B$_1$, and/or 606B$_2$ (for example but not limited to, two, three or four) can link the body 602 with one of the separable extensions 604A, 604B. The area between multiple of the perforated sections 606B$_1$, 606B$_2$ can, in some embodiments, include an adhesive material. The body 602 and the separable extension 604A still attached to the body 602 may be placed on one side of the face, and the detached separable extension 604B may be adhered to the other side of the face via use of the adhesive portion 608B, thus exposing the fixation element 610B of the detached separable extension 604B. The tube 400 can be placed over the body 602, and the separable extension 604A attached to the body 602 can be folded to cover the tube 400. Both of the fixation elements 610A, 610B may then be exposed and can be engaged with the attachment structures 216A, 216B of the patient interface 200 as described with reference to FIG. 3 to secure the patient interface 200 to the face.

In certain embodiments (and as illustrated in FIGS. 16A-16B), the tube 400 can be positioned in the perforated area (for example, the first intermediate region 605A) or adjacent the perforated area. This can facilitate quick and simple removal of the fixation structure assembly 600 from the tube 400, by tearing along the perforated sections 606B$_1$ and/or 606B$_2$. As a result, the tube 400 does not necessarily have to be removed as the fixation structure is removed, and a healthcare provider is then not required to reinsert the tube 400 following removal of the fixation structure assembly 600, reducing the number of steps required. Positioning the tube 400 in or near the perforated area can aid in enabling the fixation structure assembly 600 to be folded and/or to stick to itself. For example, this can aid in the separable extension 604A being folded over the body 602. It is to be understood that the embodiments illustrated in FIGS. 12A-12B can also facilitate the tube 400 being positioned at or adjacent to the perforated area 330A.

Figure 17A:
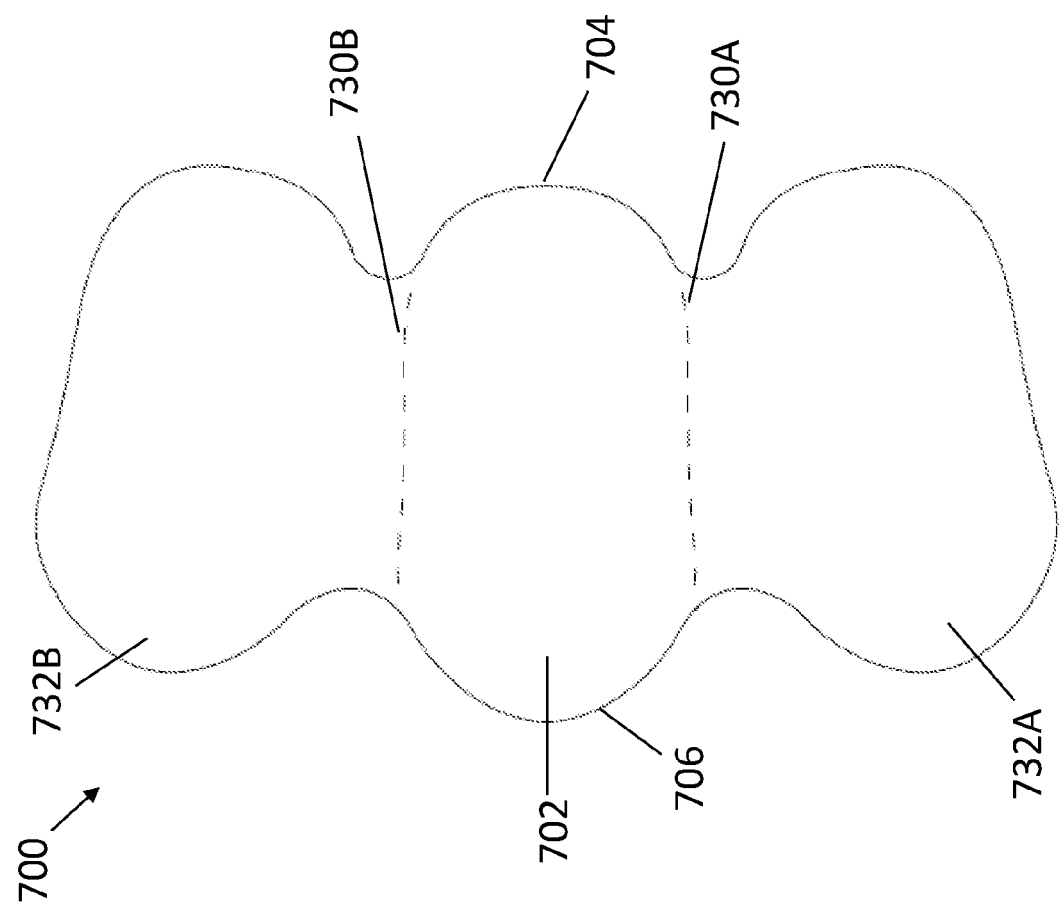

With reference to FIG. 17A, another embodiment of a fixation structure 700 is illustrated. The fixation structure 700 can include any one or more of the features of the previously described fixation structures, such as the fixation structure assembly 600 described above in connection with FIGS. 15A-16B. As illustrated, the fixation structure 700 includes a body 702 and first and second edges 704, 706. Similar to the fixation structures described above, the fixation structure 700 can include a fixation element 710 (not shown). The fixation element 710 engages with one of the attachment structures 216A, 216B to secure the patient interface 200 to the face. In some embodiments, the fixation element 710 includes a hooked pad to releasably attach to looped pads of one of the attachment structures 216A, 216B to form a hook-and-loop style connection.

The fixation structure 700 can include one or more of separable extensions 732A, 732B. In some configurations, the separable extensions 732A, 732B are formed from the same material as the body 702. In some configurations, the separable extensions 732A, 732B are formed from a different material than the body 702. The separable extensions 732A, 732B may be substantially wing-shaped. The separable extensions 732A, 732B can be at least partially linked to the body 702 by rows of perforated sections 730A, 730B. The perforated sections 730A, 730B can be torn to allow the separable extensions 732A, 732B to be separated from the body 702. In some configurations, one of the perforated sections 730A, 730B can link the body 702 with the respective one of the separable extensions 732A, 732B. In some configurations, multiple perforated sections 730A, 730B (for example, two, three or four perforated sections) can link the body 702 with the separable extensions 732A, 732B.

The arrangement of the rows of perforated sections 730A, 730B may vary. For example, the rows of perforated sections 730A, 730B make the separable extensions 732A, 732B easy for a user such as a nurse or other healthcare worker to tear from one side while being difficult for a patient to tear. This can inhibit, prevent, or make it difficult for a patient to remove the fixation structure 700 (and the attached tube 400) from the patient's face. In the configuration of the fixation structure 700 illustrated in FIG. 17B, the rows begin with a perforation on the side of the first edge 704 of the fixation structure 700 and the rows end with a non-perforation on the side of the second edge 706 of the fixation structure 700. This can facilitate tearing the fixation structure 700 from the side of the first edge 704 toward the side of the second edge 706 and/or inhibit or make it more difficult to tear the fixation structure 700 from the side of the second edge 706 toward the side of the first edge 704. In certain configurations, such as is illustrated in FIG. 17C, the rows of perforated sections 730A, 730B begin and end with a non-perforation. In some variants, the rows of perforated sections 730A, 730B begin and end with a perforation.

In some embodiments, the fixation structure 700 is configured such that the perforated sections 730A, 730B are easier to activate, for example by tearing or pulling, in one direction than the other direction. For example, in the embodiment illustrated in FIG. 17D, the perforated sections 730A, 730B include hooked, curved, or angled perforations. For example, the perforated sections 730A, 730B can be generally in the shape of the letter "J" or "L". In some embodiments, when pulling from the second edge 706 towards the first edge 704 the gap between the current perforation and the next is larger than when pulled from the first edge 704 towards the second edge 706. In some embodiments, such as is illustrated in FIG. 17E, each of the perforated sections 730A, 730B includes a first leg and a second leg, with an angle between the first and second legs of at least about 91°, at least about 100°, at least about 110°, at least about 120°, at least about 130°, at least about 145°, or at least about 160°. In some embodiments, an angle between the first and second legs is at most about 89°, at most about 80°, at most about 70°, at most about 60°, at most about 45°, or at most about 30°. In some embodiments, an angle between the first and second legs is a right angle. Other angles are contemplated. In some implementations, the first and second legs each include straight perforations.

Figure 18:
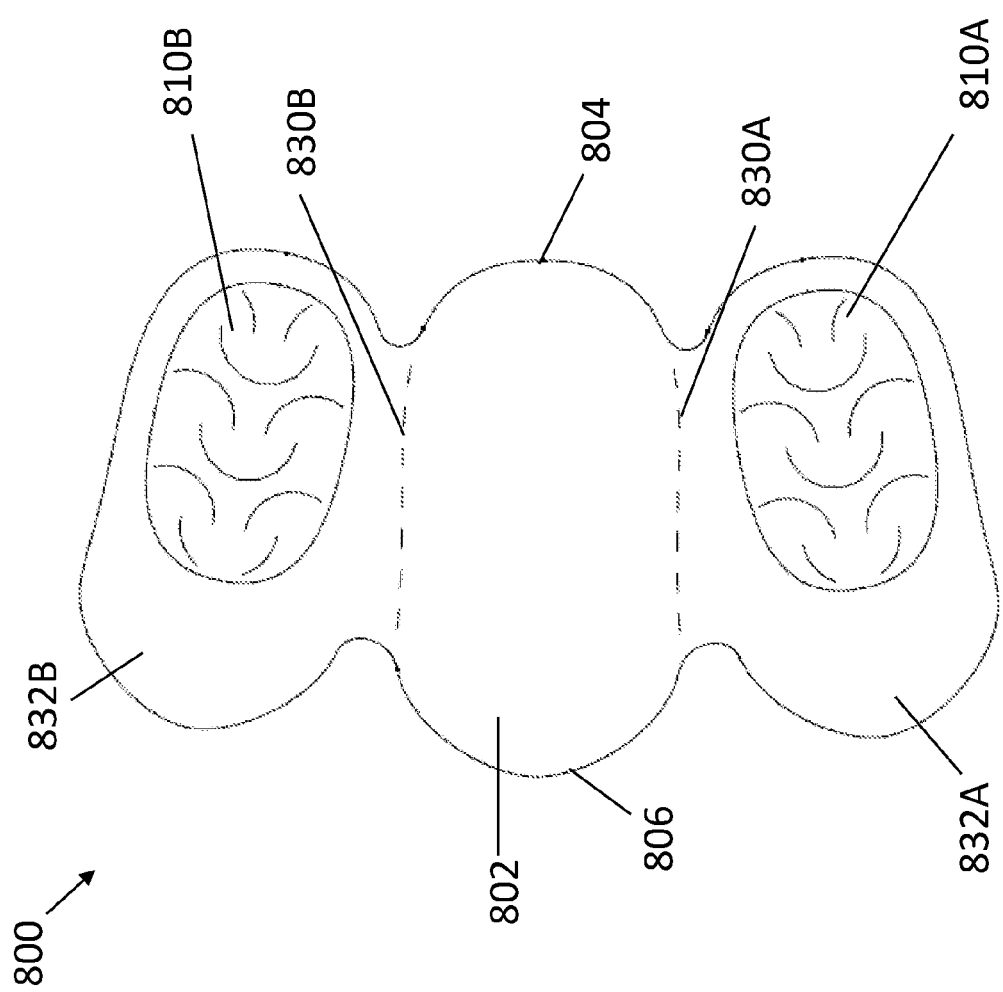
FIG. 18 illustrates example embodiments of a fixation structure.

With reference to FIG. 18, another embodiment of a fixation structure 800 is illustrated. The fixation structure 800 can include any one or more of the features of the previously described fixation structures. As illustrated, the fixation structure 800 includes a body 802 and first and second edges 804, 806. Similar to the fixation structures described above, the fixation structure 800 can include fixation elements 810A, 810B. The fixation elements 810A, 810B can engage with the attachment structures 216A, 216B to secure the patient interface 200 to the face. In some embodiments, the fixation elements 810A, 810B include hooked pads to releasably attach to looped pads of the attachment structures 216A, 216B to form a hook-and-loop style connection.

The fixation structure 800 can include one or more of separable extensions 832A, 832B. In some configurations, the separable extensions 832A, 832B are formed from the same material as the body 802. In some configurations, the separable extensions 832A, 832B are formed from a different material than the body 802. The separable extensions 832A, 832B may be substantially wing-shaped. The separable extensions 832A, 832B can be at least partially linked to the body 802 by rows of perforated sections 830A, 830B. The perforated sections 830A, 830B can be torn to allow the separable extensions 832A, 832B to be separated from the body 802. In some configurations, one of the perforated sections 830A, 830B can link the body 802 with the respective one of the separable extensions 832A, 832B. In some configurations, multiple perforated sections 830A, 830B (for example, two, three or four perforated sections) can link the body 802 with the separable extensions 832A, 832B.

Certain embodiments can facilitate maintaining the tube 400 in a patient. This can be helpful because, for example, a nasogastric or nasojejunal tube is usually a sterile component, and thus is normally discarded and replaced after being removed from a patient. By maintaining the tube 400 in the patient, the tube 400 can continue to be used, which can reduce waste and the workload associated with caring for the patient. Also, maintaining the tube 400 in the patient can reduce or avoid the difficulty and discomfort associated with fixing a nasogastric or nasojejunal tube, which is typically inserted through the nasal passage and throat and into the stomach. Insertion of a nasogastric or nasojejunal tube can be particularly challenging and uncomfortable for infants and neonates. In some embodiments, the tube 400 can be positioned in or adjacent the perforated area, which can facilitate detaching some or all of the fixation structure assembly 600 from the tube 400 without requiring that the tube 400 be removed from the patient. For example, a user, such as a nurse, can pull on the separable extension 604A or the body 602 to cause a break around the perforated area, thereby allowing the separable extension 604A and/or the body 602 to be freed from around the tube 400 while also allowing the tube 400 to remain in place (in the patient's nose). Thus, certain embodiments can provide quick and efficient removal of some or all of the fixation structure assembly 600 from the tube 400, while allowing the tube 400 to be maintained in the nose, thereby making it more comfortable for the patient, easier and quicker for the caregiver, and/or reducing the usage of nasogastric and nasojejunal tubes. All of the above is also applicable to the use of orogastric and orojejunal tubes that are inserted into the patient's mouth.

Certain embodiments have an increased area near the fixation element 610B (see FIG. 16B), such as a tab or other protrusion. The increased area can act as a bearing portion 601. The bearing portion 601 can enable a user, such as a nurse, to engage or push down on the bearing portion 601 with a finger or instrument. This can aid in disconnecting the fixation structure assembly 600 from the tube 400 and/or the patient interface 200. In certain variants, the bearing portion 601 can aid in removing the tube 400 from the patient. In some embodiments, the bearing portion 601 can help stabilize the fixation structure assembly 600 and/or can reduce the disruption of the fixation structure assembly 600 on the patient's face.

In some embodiments, the fixation structure assembly 600 includes one or more backing strips (not shown). The backing strips can include folds to allow easy removal of the backing strip to expose the adhesive fixation structure assembly 600 for use, and/or to protect the tackiness/stickiness when the fixation structure assembly 600 is not being used.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to."

Where, in the foregoing description reference has been made to integers or components having known equivalents thereof, those integers or components are herein incorporated as if individually set forth.

The disclosed methods, apparatus and systems may also be said broadly to comprise the parts, elements and features referred to or indicated in the disclosure, individually or collectively, in any or all combinations of two or more of said parts, elements or features. Further, this disclosure includes combinations of the various features, aspects, methods, properties, characteristics, qualities, attributes, elements, and the like of the various embodiments. For example, any particular feature, aspect, method, property, characteristic, quality, attribute, element, or the like in connection with an embodiment herein can be used in connection with any other embodiment herein.

Reference to any prior art in this specification is not, and should not be taken as, an acknowledgement or any form of suggestion that that prior art forms part of the common general knowledge in the field of endeavour in any country in the world.

Language of degree used herein, such as the terms "approximately," "about," "generally," and "substantially," as used herein represent a value, amount or characteristic close to the stated value, amount or characteristic that still performs a desired function or achieves a desired result. For example, the terms "generally parallel" and "substantially parallel" refer to a value, amount or characteristic that can depart from exactly parallel by less than or equal to 15 degrees, 10 degrees, 5 degrees, 3 degrees, 1 degree, 0.1 degree, or otherwise.

Some embodiments have been described in connection with the accompanying figures. The figures are drawn to scale, but such scale should not be limiting. Dimensions and proportions other than what are shown are contemplated and are within the scope of this disclosure. Distances, angles, shapes, etc. are merely illustrative and do not necessarily bear an exact relationship to actual dimensions and layout of the devices illustrated. Components can be added, removed, and/or rearranged.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

What is claimed is:

1. A fixation structure configured to fix a patient interface and a tube upon a patient, the fixation structure comprising:
    a body, the body comprising first and second regions, the first region configured to contact a portion of a patient's face and the second region configured to face outward from the patient's face; and
    first and second separable extensions, the first and second separable extensions being pivotably attached to and separable from opposing sides of the body, at least the first separable extension being completely removable from the body, the first separable extension and the second separable extension each comprising a first region and a second region, each first region of the first and second separable extensions comprising an adhesive portion and each second region of the first and second separable extensions comprising a fixation element,
    wherein the first region of the first separable extension is configured to contact another portion of the patient's face after removal of the first separable extension from the body and the second region of the first separable extension is configured to attach to the patient interface,
    wherein the second separable extension is configured to pivot relative to the body, the first region of the second separable extension is configured to contact and couple to the second region of the body to secure the tube to the body, the second region of the second separable extension is configured to attach to the patient interface.

2. The fixation structure of claim 1, wherein the adhesive portion of the second separable extension is adapted to adhere to the tube.

3. The fixation structure of claim 2, wherein the fixation element of the second region of the second separable extension comprises a first fastener adapted to attach to a complementary second fastener of the patient interface.

4. The fixation structure of claim 3, wherein the first fastener comprises one of a hook portion or a loop portion of a hook-and-loop attachment system.

5. The fixation structure of claim 4, wherein the patient interface comprises the other of the hook portion or the loop portion.

6. The fixation structure of claim 1, wherein the body comprises a first edge adapted to face towards the patient's nose or mouth, a second edge adapted to face away from the patient's nose or mouth, and opposed third and fourth edges extending between the first and second edges, wherein the first and second separable extensions are attached to the third and fourth edges of the body via perforated sections.

7. The fixation structure of claim 1, wherein the second separable extension comprises a flexible elongate section adapted to fold to encapsulate the tube.

8. The fixation structure of claim 1, wherein a shape of the body comprises rounded corners.

9. The fixation structure of claim 1, wherein the tube is a feeding tube.

10. The fixation structure of claim 1, wherein the first separable extension comprises a weakened section.

11. The fixation structure of claim 1, wherein the first separable extension is attached to the body via a perforated section.

12. The fixation structure of claim 1, wherein the fixation element of the second separable extension comprises a first fastener adapted to attach to a complementary second fastener of the patient interface, and the second separable extension is configured such that, when the second separable extension is overlapped with the body, the first fastener faces away from the patient's face.

13. The fixation structure of claim 1, wherein the second separable extension folds over the body about a pivot axis and overlaps and adheres to body.

14. The fixation structure of claim 1, wherein the second separable extension is configured to secure the tube by folding the second separable extension over the tube and adhering the second separable extension to the body.

15. The fixation structure of claim 1, wherein the adhesive portion of the second separable extension is adapted to adhere to the second region of the body.

16. The fixation structure of claim 1, wherein the second separable extension is configured to remain attached to the body.

17. The fixation structure of claim 1, further comprising two perforated sections, wherein the two perforated sections divides the fixation structure into three portions.

18. The fixation structure of claim 17, wherein each of the two perforated sections comprises two perforated lines and an intermediate region between the two perforated lines, the intermediate region configured to facilitate removal of the tube from the fixation structure.

19. The fixation structure of claim 17, wherein the two perforated sections are each positioned along a length of the fixation structure.

20. A patient interface system comprising:
 a patient interface comprising a patient-facing portion; and
 a fixation structure adapted to secure the patient interface and a tube to a face of a patient, the fixation structure comprising:
  a body comprising first and second regions, the first region configured to contact a first portion of a patient's face and the second region configured to face outward from the patient's face; and
  first and second separable extensions, the first and second separable extensions attached to and separable from opposing sides of the body, the first separable extension and the second separable extension each comprising a first region and a second region, each first region of the first and second separable extensions comprising an adhesive portion and each second region of the first and second separable extensions comprising a fixation element,
 wherein the first separable extension is completely removable from the body and the second region of the first separable extension is adapted to attach to the patient interface and the first region of the first separable extension is adapted to contact a second portion of the patient's face separate from the first portion after removal of the first separable extension from the body, and
 wherein the second separable extension is configured to pivot relative to the body, the first region of the second separable extension is configured to contact the second region of the body to secure the tube to the body, the second region of the second separable extension is adapted to attach to the patient interface.

21. The patient interface system of claim 20, wherein the body further comprises a first edge adapted to face towards the patient's nose or mouth, a second edge adapted to face away from the patient's nose or mouth, and opposed third and fourth edges extending between the first and second edges, wherein the first and second separable extensions are attached to the third and fourth edges of the body via perforated sections.

22. The patient interface system of claim 20, wherein the fixation element of the second separable extension comprises a first fastener adapted to attach to a complementary second fastener of the patient interface, and the second separable extension is configured such that, when the second separable extension is overlapped with the body, the first fastener faces away from the patient's face.

23. The patient interface system of claim 20, wherein the second separable extension is configured to secure the tube by folding the second separable extension over the tube and adhering the second separable extension to the body.

24. A fixation structure configured to fix a patient interface and a tube upon a patient, the fixation structure comprising:
 a body comprising a first side configured to contact a first location on a patient's face, the body comprising a second side configured to face outward from the patient's face; and
 a first extension attached to the body;
 a second extension attached to the body, each of the first extension and the second extension configured to be selectively separable from the body;
 wherein, in use, the first extension is separated from the body, wherein a first side of the first extension is configured to contact a second location on the patient's face spaced from the first location, wherein a second side of the first extension is attached to the patient interface;
 wherein, in use, the second extension is pivoted relative to the body such that a first side of the second extension is attached to the second side of the body to secure the tube to the body, and wherein the second side of the second extension is attached to the patient interface.

25. The fixation structure of claim 24, wherein the body further comprises a first edge adapted to face towards the patient's nose or mouth, a second edge adapted to face away from the patient's nose or mouth, and opposed third and fourth edges extending between the first and second edges, wherein the first and second extensions are attached to the third and fourth edges of the body via perforated sections.

26. The fixation structure of claim 24, wherein the second extension comprises a first fastener adapted to attach to a complementary second fastener of the patient interface, and the second extension is configured such that, when the second extension is overlapped with the body, the first fastener faces away from the patient's face.

27. The fixation structure of claim 24, wherein the second extension is configured to secure the tube by folding the second extension over the tube and adhering the second extension to the body.

28. The fixation structure of claim 24, wherein the first side of the second extension comprises an adhesive portion adapted to adhere to the tube.

29. The fixation structure of claim 24, wherein a shape of the body comprises rounded corners.

30. The fixation structure of claim 24, wherein the tube is a feeding tube.

31. The fixation structure of claim 24, wherein the first side of the second extension comprises an adhesive portion adapted to adhere to the second side of the body.

* * * * *